(12) United States Patent
McKinley et al.

(10) Patent No.: US 8,439,835 B1
(45) Date of Patent: May 14, 2013

(54) SYSTEM AND METHOD FOR DIAGNOSIS AND MANAGEMENT OF SEPSIS

(75) Inventors: Bruce A. McKinley, Alvin, TX (US);
Frederick A. Moore, Fulshear, TX (US);
R. Matthew Sailors, Houston, TX (US);
Laure J. Moore, Houston, TX (US); S. Rob Todd, Houston, TX (US); Krista L. Turner, Houston, TX (US); Joseph F. Sucher, Katy, TX (US)

(73) Assignee: Bruce A. McKinley, Houston, TX (US)

( * ) Notice: Subject to any disclaimer, the term of this patent is extended or adjusted under 35 U.S.C. 154(b) by 821 days.

(21) Appl. No.: 12/495,023

(22) Filed: Jun. 30, 2009

Related U.S. Application Data

(60) Provisional application No. 61/133,469, filed on Jun. 30, 2008.

(51) Int. Cl.
*A61B 5/00* (2006.01)

(52) U.S. Cl.
USPC .......................................... 600/301; 128/920

(58) Field of Classification Search ........................ None
See application file for complete search history.

(56) References Cited

U.S. PATENT DOCUMENTS

| 6,047,259 | A * | 4/2000 | Campbell et al. ................. 705/3 |
| 6,148,814 | A | 11/2000 | Clemmer |
| 6,682,481 | B2 | 1/2004 | McKinley |
| 2002/0087358 | A1 * | 7/2002 | Gilbert ............................... 705/2 |
| 2005/0164238 | A1 * | 7/2005 | Valkirs et al. ..................... 435/6 |
| 2008/0091088 | A1 * | 4/2008 | Kiani ............................. 600/301 |
| 2009/0149724 | A1 * | 6/2009 | Mark et al. ..................... 600/301 |

OTHER PUBLICATIONS

Balk, Robert A. Optimum Treatment of Severe Sepsis and Septic Shock: Evidence in Support of the Recommendations. Disease-A-Month, Apr. 2004; 50: 168-213.*
Dellinger et al., "Surviving Sepsis Campaign: International guidelines for management of severe sepsis and septic shock: 2008", *Crit Care Med.*, vol. 36, No. 1, pp. 296-327.
Dellinger et al., "Surviving Sepsis Campaign guidelines for management of severe sepsis and septic shock", *Crit Care Med*, vol. 32, No. 3, pp. 858-873, 2004.
East et al.l, "Efficacy of Computerized Decision Support for Mechanical Ventilation: Results of a Prospective Multi-Center Randomized Trial", *AMIA, Inc*, 1091-8280/99/$5.00, pp. 251-255, 1999.
McKinley et al., "Computerized Decision Support for Mechanical Ventilation of Trauma Induced ARDS: Results of a Randomized Clinical Trial", *J Trauma*, vol. 50, No. 3, pp. 415-425, 2001.

(Continued)

*Primary Examiner* — Bill Thomson
*Assistant Examiner* — Davin K Sands
(74) *Attorney, Agent, or Firm* — Sprinkle IP Law Group

(57) ABSTRACT

Embodiments of systems and methods for providing protocols for administering an aspect of care are presented. Specifically, certain embodiments relate to a sepsis diagnosis and management protocol which may have been segmented according to the severity of the sepsis, where the care directives provided by the differing segments of the protocol will be of differing intensity or invasiveness based upon the severity of the patient's disease. Embodiments of such protocols may be implemented in conjunction with computer systems to aid in providing that aspect of care in conjunction with a particular patient.

12 Claims, 28 Drawing Sheets

OTHER PUBLICATIONS

Morris, A., "Developing and Implementing Computerized Protocols for Standardization of Clinical Decisions", *Ann Intern Med.*, vol. 132, No. 5, pp. 373-383, 2000.

Morris et al., "A replicable method for blood glucose control in critically Ill Patients", *Crit Care Med.*, vol. 36, No. 6, pp. 1787-1795, 2008.

Morris, A., "Treatment algorithms and protocolized care", *Curr Opin Crit Care*, vol. 9:236-240, 2003.

Sucher et al., "Computerized Clinical Decision Support: A Technology to Implement and Validate Evidence Based Guidelines", *J. Trauma*, 64:520-537, 2008.

Vogelzang, et al., "Design and implementation of GRIP: a computerized glucose control system at a surgical intensive care unit", *BMC Medical Informatics and Decision Making*, 5:38, pp. 1-10, 2005.

* cited by examiner

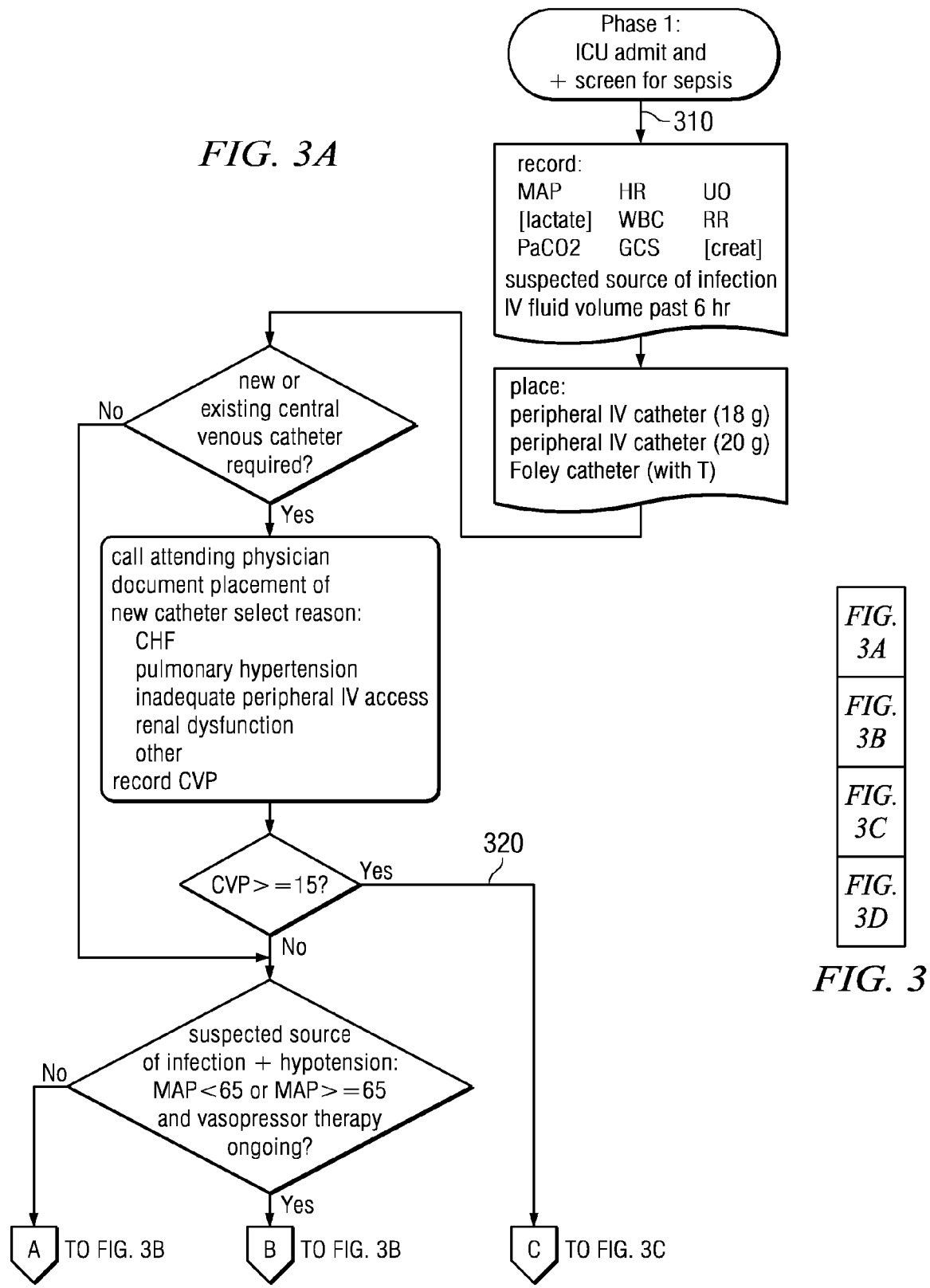

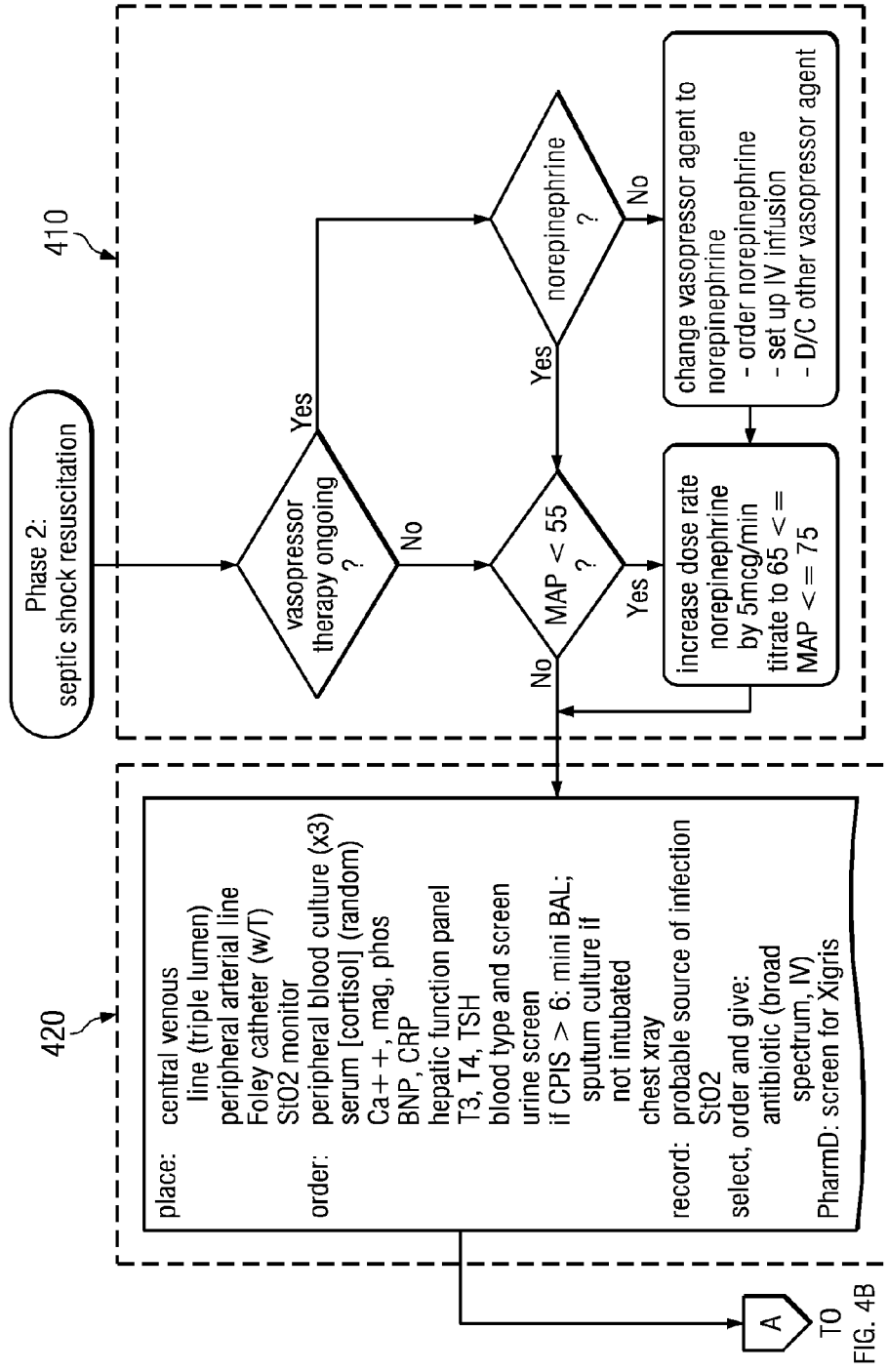

SICU Bedside Nurse
SIRS score current heart rate _____   time _____
T min _____   time _____
T max _____   time _____
current resp rate _____   time _____
latest WBC count _____   date, time _____ patient label

10232007

| points | 0 | 1 | 2 | 3 | 4 |
|---|---|---|---|---|---|
| heart rate (bpm) | 70 - 109 | | 55 - 69<br>110 - 139 | 40 - 54<br>140 - 179 | ≤ 39<br>≥ 180 |
| T (°C) min<br>max<br>T (°F) min<br>max | 36 - 38.4<br>96.8 - 101.1 | 34 - 35.9<br>38.5 - 38.9<br>93.1 - 96.6<br>101.2 - 102.0 | 32 - 33.9<br>89.6 - 93.0 | 30 - 31.9<br>39 - 40.9<br>86 - 89.5<br>102.1 - 105.6 | ≤ 29.9<br>≥ 41<br>≤ 85.9<br>≥ 105.7 |
| resp rate (br / min) | 12 -24 | 10 -11<br>25 - 34 | 6 - 9 | 35 - 49 | ≤ 5<br>≥ 50 |
| latest WBC (kcell / mm$^3$) | 3 - 14.9 | 15 - 19.9 | 1 - 2.9<br>20 - 39.9 | | < 1<br>≥ 40 |
| score (total points) | | | | | |

If SIRS score ≥ 4, then notify SICU Nurse Practitioner to complete sepsis screening form.

☐ SICU
☐ overflow   ☐ MICU   ☐ NICU   ☐ CCU

Completed by: _____, RN   Date / time: _____

Performance improvement review by SICU Medical Director or designee:

☐ sepsis (Phase 1)   ☐ severe sepsis (Phase 2)   ☐ septic shock (Phase 2)

Start sepsis management protocol   ☐ Yes   ☐ No

Comments: _____
_____
_____

Signature: _____, MD   Date / time: _____

| SICU Nurse Practitioner Sepsis Screening | | | | | | | |
|---|---|---|---|---|---|---|---|
| 1. Vascular access? | | | | Yes | No | | Suspicion of: |
| type | dialysis | triple / quad | PICC | port | tunneled | other (IV, art) | line infection? |
| date placed | | | | | | | |
| site | | | | | | | Yes    No |
| local finding | | | | | | | |
| blood culture finding | | | | | | | |

| 2. Clinical pulmonary infection score (CPIS) | | | |
|---|---|---|---|
| Variable | | points  score | pneumonia? |
| temperature (°C) | time (hhmm) | | Yes    No |
| 36.5 - 38.4 | | 0 | Intubated / mech vent support? |
| 38.5 - 38.9 | | 1 | |
| > 39.0 or < 36.0 | | 2 | |
| blood leukocyte count (# per mm$^3$) | time (hhmm) | | Yes    No |
| 4,000 - 11,000 | | 0 | date intubated: |
| < 4,000 or > 11,000 | | 1 | |
| tracheal secretions | time (hhmm) | | |
| small | | 0 | |
| moderate | | 1 | |
| large | | 2 | |
| purulent (add 1 point if purulent) | | +1 | |
| oxygenation (PaO$_2$/FiO$_2$) | time (hhmm) | | |
| ≤ 240 or presence of ARDS | | 0 | |
| < 240 and absence of ARDS | | 2 | |
| chest radiograph | time (hhmm) | | |
| no infiltrate | | 0 | |
| patchy or diffuse infiltrate | | 1 | |
| localized infiltrate | | 2 | |

| 3. Abdomen | | | |
|---|---|---|---|
| recent abdominal surgery? | Yes | No | abdominal infection? |
| abdominal pain? | Yes | No | |
| abdominal distention? | Yes | No | Yes    No |
| purulent drainage from surgical drains? | Yes | No | |
| intolerance to enteral nutrition? | Yes | No | |

| 4. Skin / soft tissue | | | |
|---|---|---|---|
| erythema / drainage from other surgical site? | Yes | No | cellulitis / soft tissue infection? |
| site | | | Yes    No |

| 5. Urinary tract | | | |
|---|---|---|---|
| urinary catheter? | Yes | No | UTI? |
| date placed | | | |
| latest urinalysis / urine culture results | | | Yes    No |

| 6. Other site | | | |
|---|---|---|---|
| site | | | other infection? |
| Completed by: _____ , NP | Date / time: _____ | | Yes    No |

*FIG. 12B*

SYSTEM AND METHOD FOR DIAGNOSIS AND MANAGEMENT OF SEPSIS

RELATED APPLICATIONS

This application claims priority to U.S. Provisional Patent Application No. 61/133,469 filed Jun. 30, 2008 entitled "System and Method for Diagnosis and Management of Sepsis" by McKinley et. al, which is hereby fully incorporated by reference herein for all purposes.

TECHNICAL FIELD

This invention relates generally to the field of medical informatics, biomedical engineering and surgical intensive care. More specifically, embodiments of the present invention relate to clinical decision support using rule-based systems for the care of patients who are septic. Even more particularly, embodiments of the present invention relate to rule-based systems for the care of patients who are septic which may be implemented in a computerized medical environment.

BACKGROUND

Sepsis is a serious medical condition characterized by a whole-body inflammatory state and the presence of a known or suspected infection. The body may develop this inflammatory response to microbes in the blood, urine, lungs, skin, or other tissues. Sepsis is characterized by evidence of acute inflammation present throughout the entire body, and is, therefore, frequently associated with higher than normal heart rate, fever or lower than normal temperature and elevated white blood cell count (leukocytosis) or lower than normal white blood cell count.

The modern concept of sepsis is that the host's immune response to the infection causes most of the symptoms of sepsis, resulting in hemodynamic consequences and damage to organs. This host response has been termed systemic inflammatory response syndrome (SIRS) and is characterized by hemodynamic compromise and metabolic derangement. Outward physical symptoms of this response frequently include a high heart rate, high respiratory rate, elevated white blood cell count, and elevated or lowered body temperature. Sepsis is differentiated from SIRS by the presence of a pathogen. Without infection the above symptoms may not be classified as sepsis, only SIRS.

Severe sepsis occurs when sepsis leads to organ dysfunction, low blood pressure (hypotension), or insufficient blood flow (hypoperfusion) to one or more organs (causing, for example, lactic acidosis, decreased urine production, or altered mental status). Sepsis can lead to septic shock, multiple organ dysfunction syndrome (sometimes known as multiple organ failure) and death. Organ dysfunction may result from sepsis-induced hypotension and diffuse intravascular coagulation, among other things.

In the United States, sepsis is the second-leading cause of death in non-coronary intensive-care unit (ICU) patients, and the tenth-most-common cause of death overall according to data from the Centers for Disease Control and Prevention (the first being multiple organ failure). Sepsis is common and also more dangerous in elderly, immunocompromised, and critically-ill patients. It occurs in 1-2% of all hospitalizations and accounts for as much as 25% of ICU bed utilization. It is a major cause of death in intensive-care units worldwide, with mortality rates that currently range from 20% for sepsis to 40% for severe sepsis to >60% for septic shock.

Sepsis is usually treated in the intensive care unit with intravenous fluids and antibiotics. If fluid replacement is insufficient to maintain blood pressure, specific vasopressor drugs can be used. Artificial ventilation and dialysis may be needed to support the function of the lungs and kidneys, respectively. To guide therapy, a central venous catheter and an arterial catheter may be placed to monitor intravascular pressures. Sepsis patients require preventive measures for deep vein thrombosis, stress ulcers and pressure ulcers, unless other conditions prevent this. Some patients might benefit from tight control of blood sugar levels with insulin (targeting stress hyperglycemia), low-dose corticosteroids or activated drotrecogin alfa (recombinant protein C).

Presently there is great variability in the diagnosis and management of sepsis generally across health care institutions, between and among physicians, and between and among differing patients, even within the same health care institution. Additionally, mortality and cost of intensive care unit (ICU) care of patients with sepsis remain prohibitive. To apply current standard of care to sepsis patients typically requires frequent or constant bedside presence of an expert physician to guide decision making for monitoring or therapeutic interventions. Available evidence based guideline and other literature evidence for management of sepsis are difficult for the bedside clinician to use to direct the care process for the individual patient, and ad hoc treatment with haphazard application of literature evidence or guideline recommendations is common.

Consequently, it is desired to substantially ameliorate these problems.

SUMMARY

Embodiments of systems and methods for providing a sepsis diagnosis and management protocol are presented. Specifically, certain embodiments of the sepsis diagnosis and management protocol may have been derived from currently available guidelines and literature evidence where the protocol is intended to be utilized to identify a patient with sepsis and direct and determine a logic path of care for that particular patient. Specifically, embodiments of the sepsis diagnosis and management protocol may be segmented according to the severity of the sepsis, where the care directives provided by the differing segments of the protocol will be of differing intensity or invasiveness based upon the severity of the patient's disease. These segments may correspond to a set of rules and logic which are clinically distinct, independent processes that are part of the overall aspect of care where the sets of rules and associated logic may be logically distinct within the protocol. Within such a segment, the set of rules may have thresholds or interventions changed without affecting the basic process or other segments. A segment may be useful in other aspects of care. Thus, the segment could be used to manage that process for another patient or as part of another aspect of care. The modularity of certain segments permits edition, update and other change without extensive revision to a protocol, and thereby permits immediate incorporation of new guideline or literature evidence to maintain clinical currency and improved standard of care for all patients.

Embodiments of such a sepsis diagnosis and management protocol may therefore be a rule based protocol developed based on a number of sources, including any combination of published guidelines, literature evidence or expert consensus opinion and ongoing protocol analysis.

Specifically, embodiment of a protocol presented herein is designed to direct clinician assessment of the severity of sepsis according to specific criteria for sepsis, severe sepsis and septic shock, to direct hemodynamic monitoring that is appropriate for the sepsis severity and related hemodynamic instability that is present, to prescribe immediate IV fluid administration in calibrated volumes to regain hemodynamic stability defined as numeric blood pressure and heart rate measurement thresholds for intervention, to prescribe immediate antibiotic agent therapy that is appropriate for the individual patient and suspected source of infection, and to direct specific interventions to maintain hemodynamic stability and systemic oxygenation using specific measurements and numeric thresholds for intervention for at least the $1^{st}$ 24 ICU hours after diagnosis of sepsis.

The efficacy of embodiments of the present invention is demonstrable. In a time period of 15 months, 172 patient encounters for sepsis, severe sepsis and septic shock were managed using this protocol. Summary demographics and outcomes are described in the table below. As can be seen, patients with severe sepsis and septic shock have survival rates that are much less than patients with sepsis, but much greater than 50% that is a commonly cited survival rate. Overall, sepsis survival rate utilizing embodiments of the protocols described herein was 72%. In the year after sepsis management protocol introduction, mortality rate decreased from 35 to 23%.

|  | Sepsis (n = 30) | Severe sepsis (n = 101) | Septic shock (n = 41) |
| --- | --- | --- | --- |
| Age (mean ± SEM) | 54 ± 3 | 60 ± 2 | 61 ± 3 |
| gender (male) | 16 (52%) | 47 (47%) | 16 (39%) |
| MAP t = 0 (mmHg) (mean ± SEM) | 85 ± 2 | 81 ± 1 | 66 ± 2 |
| [lactate] t = 0 (mM) (mean ± SEM) | 1.4 ± 0.1 | 3.2 ± 0.4 | 4.2 ± 0.5 |
| ICU free days (mean ± SEM) | 20.1 ± 1.4 | 15.0 ± 1.0 | 12.1 ± 1.6 |
| ICU survival | 31 (100%) | 85 (85%) | 27 (66%) |

MAP t=0, mean arterial pressure at start of sepsis management protocol; [lactate] t=0, blood lactate concentration at start of sepsis management protocol; ICU free days, 28 minus number of days spent in ICU after sepsis diagnosis or 0 if death in ICU before 28 days after sepsis diagnosis; ICU survival, survival extending beyond number of days spent in ICU after sepsis diagnosis In some cases, embodiments of a protocol for an aspect of care, such as for the diagnosis and management of sepsis may be implemented in a computerized system. These computerized protocols are capable of directing complex care processes to provide evidence based care that is comprehensive, individualized, appropriately timed, and based on standardized bedside clinical decisions that are replicable among patients. For sepsis management, a complex process, the potential impact of guideline recommendations, literature evidence and protocol implementation is likely to be realized using the computerized protocol.

The efficacy of implementing embodiments of the protocol described herein is also demonstrable. In a 3 month period patients had sepsis diagnosed and the computerized protocol was used by bedside clinicians to manage each patient's sepsis encounter. Computerized protocol compliance by bedside clinicians was 90% (833 of 930 computerized protocol generated instructions to bedside clinicians) during these three months. Early effects of computerized sepsis management protocol implementation are indicated below:

|  | Sepsis (n = 7) | Severe sepsis (n = 5) | Septic shock (n = 14) |
| --- | --- | --- | --- |
| ICU free days (mean ± SEM) | 19.4 ± 3.1 | 16.4 ± 1.9 | 12.0 ± 3.0 |
| ICU survival | 7 (100%) | 21 (84%) | 12 (79%) |

ICU free days, 28 minus number of days spent in ICU after sepsis diagnosis or 0 if death in ICU before 28 days after sepsis diagnosis; ICU survival, survival extending beyond number of days spent in ICU after sepsis diagnosis.

One embodiment of a protocol for sepsis management may be segmented as a process for management of relatively less severe sepsis and a process for management of relatively more severe sepsis (including septic shock). The process for management of less severe sepsis may comprise a rule set for low risk patient monitoring (e.g. non invasive blood pressure, heart rate) and for interventions with lesser therapeutic intensity and risk (e.g. IV fluid dose volumes) that are sufficient to maintain adequate hemodynamic function as measured by minimally invasive monitors and according to threshold rules for intervention. In a (hospital) patient setting for which onset of sepsis is deemed likely and in which low risk monitors (e.g. non invasive blood pressure, heart rate) are routinely used, the process for management of less severe sepsis may comprise a set of rules to detect the onset or existence of sepsis. The process for management of less severe sepsis may also comprise a set of threshold rules to detect development of more severe sepsis or septic shock and for transition to the process for management of severe sepsis or septic shock. The process for management of severe sepsis or septic shock may comprise a rule set for more invasive patient monitoring (e.g. invasive intravascular blood pressure) and for interventions with greater therapeutic intensity and risk (e.g. vasopressor drug therapy) that are sufficient to maintain adequate hemodynamic function as measured by invasive monitors and according to threshold rules for intervention.

These, and other, aspects of the invention will be better appreciated and understood when considered in conjunction with the following description and the accompanying drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE DRAWINGS

The drawings accompanying and forming part of this specification are included to depict certain aspects of the invention. A clearer impression of the invention, and of the components and operation of systems provided with the invention, will become more readily apparent by referring to the exemplary, and therefore nonlimiting, embodiments illustrated in the drawings, wherein identical reference numerals designate the same components. Note that the features illustrated in the drawings are not necessarily drawn to scale.

FIG. 9A is a representation of one embodiment of a scoring method for use with the protocol for sepsis diagnosis and management.

FIG. 9B is a representation of one embodiment of a scoring method for use with the protocol for sepsis diagnosis and management.

Figure 12B:
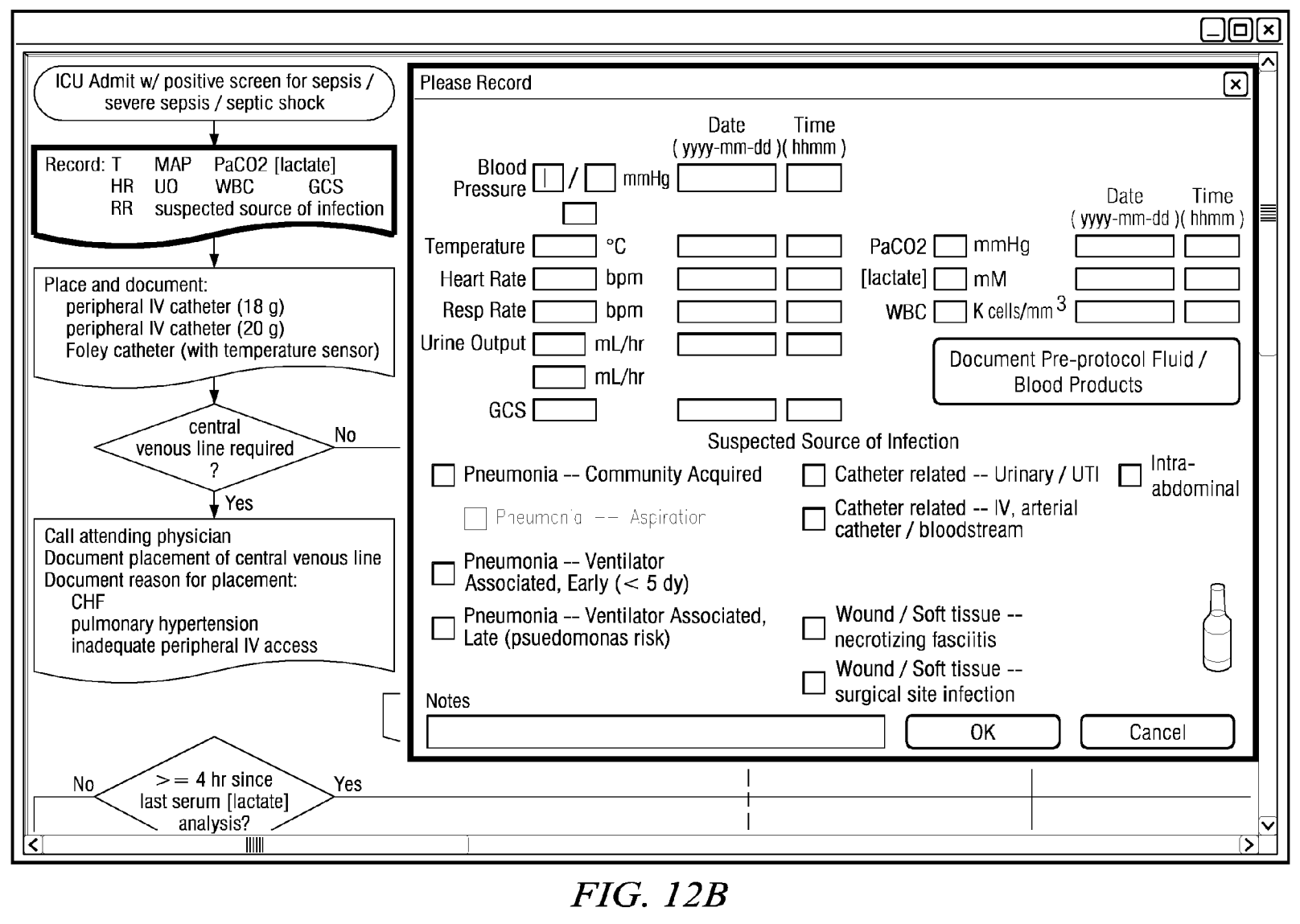

FIGS. 12A-12E are representations of embodiments of interfaces which may be utilized by a system for a computerized implementation of a protocol.

DETAILED DESCRIPTION

Figure 1:
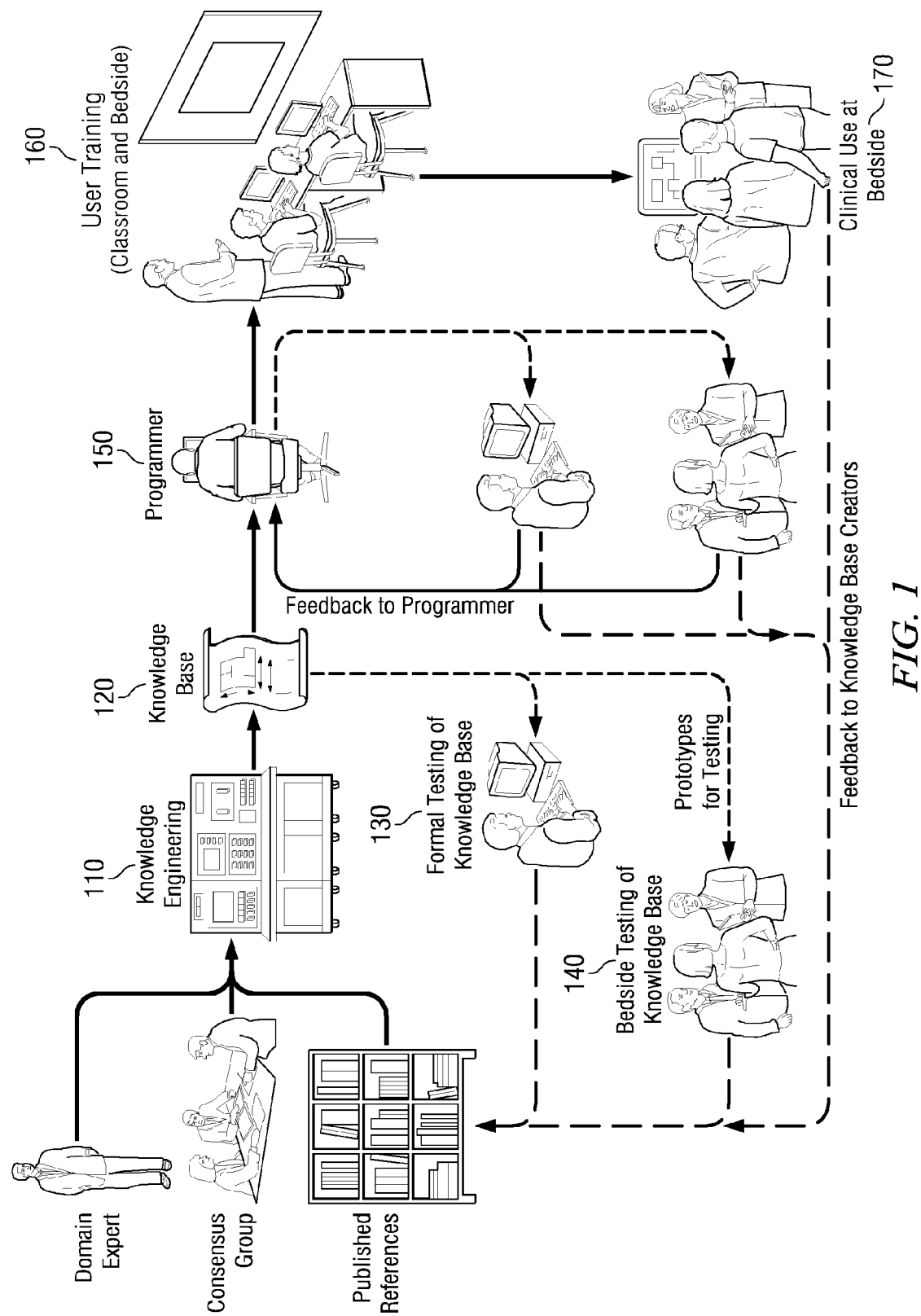
FIG. 1 is an illustration of one embodiment of a process for development and implementation of a protocol for clinical care.

The invention and the various features and advantageous details thereof are explained more fully with reference to the nonlimiting embodiments that are illustrated in the accompanying drawings and detailed in the following description. Descriptions of well known starting materials, processing techniques, components and equipment are omitted so as not to unnecessarily obscure the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure. Embodiments discussed herein can be implemented in suitable computer-executable instructions that may reside on a computer readable medium (e.g., a HD), hardware circuitry or the like, or any combination.

Before discussing specific embodiments, embodiments of a hardware architecture for implementing certain embodiments is generally described herein and will be discussed in more detail later. One embodiment can include one or more computers communicatively coupled to a network. As is known to those skilled in the art, the computer can include a central processing unit ("CPU"), at least one read-only memory ("ROM"), at least one random access memory ("RAM"), at least one hard drive ("HD"), and one or more input/output ("I/O") device(s). The I/O devices can include a keyboard, monitor, printer, electronic pointing device (such as a mouse, trackball, stylus, etc.), or the like. In various embodiments, the computer has access to at least one database over the network.

ROM, RAM, and HD are tangible computer readable medium for storing computer-executable instructions executable by the CPU. Within this disclosure, the term "computer-readable medium" is not limited to ROM, RAM, and HD and can include any type of data storage medium that can be read by a processor. In some embodiments, a tangible computer-readable medium may refer to a data cartridge, a data backup magnetic tape, a floppy diskette, a flash memory drive, an optical data storage drive, a CD-ROM, ROM, RAM, HD, or the like.

At least portions of the functionalities or processes described herein can be implemented in suitable computer-executable instructions. The computer-executable instructions may be stored as software code components or modules on one or more computer readable media (such as non-volatile memories, volatile memories, DASD arrays, magnetic tapes, floppy diskettes, hard drives, optical storage devices, etc. or any other appropriate computer-readable medium or storage device). In one embodiment, the computer-executable instructions may include lines of complied C++, Java, HTML, or any other programming or scripting code.

Additionally, the functions of the disclosed embodiments may be implemented on one computer or shared/distributed among two or more computers in or across a network. Communications between computers implementing embodiments can be accomplished using any electronic, optical, radio frequency signals, or other suitable methods and tools of communication in compliance with known network protocols.

As used herein, the terms "comprises," "comprising," "includes," "including," "has," "having" or any other variation thereof, are intended to cover a non-exclusive inclusion. For example, a process, process, article, or apparatus that comprises a list of elements is not necessarily limited to only those elements but may include other elements not expressly listed or inherent to such process, process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," "in one embodiment."

A brief discussion of context particularly with respect to treatment of sepsis may now be helpful. As discussed above, there is great variability in the diagnosis and management of sepsis. However, recent data gives significant indications that the early treatment of sepsis according to evidence based guidelines is effective in improving mortality rates and decreasing the length of intensive care unit (ICU), or hospital, stays for these patients. These evidence based guidelines (for example, 'Surviving Sepsis Campaign: Guidelines for Management of Severe Sepsis and Septic Shock' and its revision 'Surviving Sepsis Campaign: International Guidelines for Management of Severe Sepsis and Septic Shock: 2008' (Dellinger et al. Crit Care Med 2008)), while desirable in the abstract, are often difficult, if not impossible, to use to help guide care of the individual patient in a particular health care institution. While many reasons contribute to this difficulty, one of the major reasons has to do with the generality of these guidelines. These guidelines provide neither patient specific directives nor explicit directives or instructions for individual patient care by the bedside clinician. Additionally, and along the same lines, for bedside clinicians (which in many cases, may not be physicians, but instead may be physician extenders, nurses or clinician assistants) these guidelines are too many and too complex to recall, or too general to provide sufficient guidance in individual cases.

While certain attempts have been made to fashion guidelines, these attempts have resulted in significant clinician frustration due to complexity of the disease and therapy process, and due to the need for specific, timely instructions for measurements of physiologic functions and for interventions to treat sepsis using the best available information. What is desired then, is a sepsis diagnosis and management protocol that is based on the currently available evidence and guidelines and that can provide specific instructions to a bedside clinician for timely care of the individual patient based on patient specific information. Protocols are precise, detailed plans for management or study of a medical problem or regimen of therapy. Protocols provide specific instruction for individual clinical decisions, and, importantly, elicit the same decision from different clinicians. Protocols standardize decision making among bedside clinicians, and make decisions for specific interventions replicable among patients. Furthermore, it is desired that such sepsis diagnosis and management protocols may be implemented on computerized systems to allow the automated requests for, or gathering of, measurements associated with the patient, the patient's clinical status, and the presentation of protocol derived instructions for care specifically tailored for the individual patient in accordance with both the patients' information and the sepsis diagnosis and management protocol.

To that end, attention is now directed to the systems and methods of the present invention. Embodiments of these systems and methods provide a sepsis diagnosis and management protocol which has been derived from currently available guidelines and evidence where the protocol is intended to be utilized to identify a patient with sepsis (including severe sepsis or septic shock) and direct and determine a logic path of care for that particular patient. Specifically, embodiments of the sepsis diagnosis and management protocol may be segmented according to the severity of the sepsis, where the care directives provided by the differing segments of the protocol will be of differing intensity or invasiveness based upon the immediate severity of the individual patient's disease. For example, one segment may comprise rules associated with all cases of sepsis and some cases of severe sepsis and another segment may comprise rules associated with some cases of severe sepsis including cases of septic shock, where the rules to apply to the care of a particular patient may be determined according to one or the other of the segments based upon that specific patient's condition. Rules of the protocol may also be segmented based upon any number of other criteria, such as for example clinical dependency or independency or the like.

Embodiments of such a sepsis diagnosis and management protocol may therefore be a rule based protocol developed based on a number of sources, including any combination of published guidelines, literature evidence or expert consensus opinion, and ongoing analysis of protocol performance. Such a protocol may comprise rules including instructions, interventions, requests for patient specific information, thresholds for measurements etc. organized in a logical sequence that may accommodate bedside workflow, thereby providing patient based rules for care that are based on patient specifics, including patient condition and responses to interventions, and which are replicable among different patients. The modular design of embodiments of these types of protocols permit modifications to incorporate new guideline or literature evidence, change of threshold or therapy intervention, or to accommodate specific hospital or care unit workflow.

The application, revision, etc. of embodiments of a sepsis diagnosis and management protocol may therefore be facilitated by the implementation of embodiments of these protocols as a computer based system such that requests for information, instructions for interventions or the presentation of information related to other rules associated with protocol may be delivered via computer to any interface, such as a computer screen, personal digital assistant (PDA), laptop, cell phone screen, speaker, etc. The logic for selecting a certain rule of the protocol to apply, the time certain actions occurred, patient-specific data (as non-limiting examples, demographics, criteria, related measurements, etc.) and patient responses to specific interventions may be recorded and the next rule in the protocol to implement with respect to that patient may be determined in conjunction with the protocol as applied to that specific patient's information. Thus, the protocol will tailor the care administered to the current conditions of the individual patient by applying rules of the protocol selected based upon that patient's immediate condition.

As the rules (for example, instructions related to interventions, request to obtain or enter measurements, etc.) issued through the interface are tailored to the specific patient being cared for, the bedside presence of an expert physician for stepwise decision making throughout the protocol care process is not necessarily required. In fact, in certain embodiments such a computer based protocol system may be connected to one or more medical devices from which patient information (including, for example, medical or demographic data) may be obtained or rules implemented (for example, adjustment of amount of medication being delivered through an intravenous line, etc.) such that one or more rules associated with the protocol may occur substantially without the involvement of a bedside clinician. Additionally, as the data is recorded during the administration of care to the patient according to the protocol it can be retrospectively analyzed to optimize and improve the care process, including the protocol itself.

Turning now to FIG. 1, it may be helpful to give an overview of the lifecycle of protocols, including those protocols for the diagnosis and management of sepsis. Accordingly, FIG. 1 depicts one embodiments of a method for development and use of a protocol for the diagnosis and management of sepsis. More specifically, a knowledge base for the diagnosis and management of sepsis may be developed at step 110. The development of such a knowledge base may entail the review of published references, guidelines journal articles or other documents related to the diagnosis and treatment of sepsis, obtaining information from experts in the area of diagnosis and management of sepsis, obtaining information from one or more consensus groups regarding diagnosis and management of sepsis or obtaining information from any other desired source regarding the diagnosis and management of sepsis.

Once this information is obtained, it can be distilled into a knowledge base comprising the protocol, where the knowledge base comprises a protocol including a set of rules organized according to a logical sequence. This knowledge base may be tested at step 120 and the knowledge obtained from testing used to develop/revise the knowledge base at step 110. The testing of such a knowledge base may comprise a review or other testing procedures done in a patient independent manner at step 130, or may comprise testing of the protocol in conjunction with patient care or treatment at step 140.

At some point then, at step 150 the protocol may be given to a programmer to develop a computer system implemented version of the protocol. This computer implemented protocol may be configured to guide a clinician or other user through the implementation of a protocol such that requests for information, instructions for interventions or the presentation of information related to other rules associated with protocol may be delivered via computer to an interface and patient-specific data including patient responses to specific interventions or patient specific measurements may be obtained through an interface and rules of the protocol evaluated. The computer implemented protocol may also be tested at step 120 and the knowledge obtained from testing used to develop/revise the knowledge base at step 110. The testing of such a knowledge base may comprise a review or other testing procedures done in a patient independent manner at step 130, or may comprise testing of the protocol in conjunction with patient care or treatment at step 140.

Once the protocol is implemented in a computer system at step 150, before implementation in conjunction with an actual patient, at step 160, it may be desirable to train clinicians with respect to the protocol or the computer system on which the protocol is implemented. Thereafter, the computer implemented protocol may be used in a clinical setting at step 170, for example at the patient's bedside such that the patient's care is based on the protocol. Any feedback generated from the use of the protocol in conjunction with actual patient care base may be also used to develop/revise the knowledge base at step 110.

Figure 2:
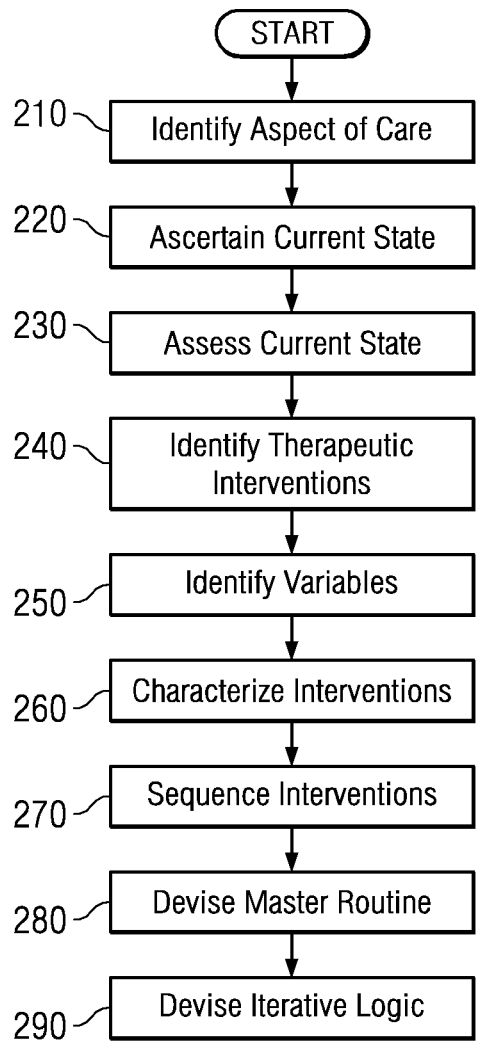
FIG. 2 is a flow diagram representing one embodiment of a method for deriving a protocol.

As can be seen then, in certain embodiments, initially a protocol may be created from the extant literature, including any articles or guidelines, and the knowledge of clinicians and consensus groups formed with respect to that aspect of care. FIG. 2 depicts a flow diagram for a method of creating such a protocol. Initially, before creating a protocol, at step 210 an aspect of care for which the protocol is to apply can be identified. In the example embodiments illustrated herein, the aspect of care is sepsis diagnosis and management, however, the use of this example should not be construed as a constraint upon other embodiments of the present invention which may be effectively utilized with other aspects of care.

Once the desired aspect of care for which a protocol is to be created is identified, the current state of that aspect of care may be ascertained at step 220. Ascertaining the current state of that aspect of care may, in general, comprise a search of the literature, querying experts in that aspect of care, a review of articles, guidelines or other literature pertinent to that aspect of care. The experts queried may, for example, be local experts associated with, for example, a particular health care institution or setting or unit within a health care institution (for example, a hospital, an ICU within a hospital, etc.), such that expert knowledge pertaining to the current state of the aspect of care with respect to a particular location may ascertained.

The depth or nature of this review may depend, at least in part, on the aspect of care. For example, in the case of ascertaining the current state of care for sepsis diagnosis and management, peer reviewed literature may be reviewed along with querying local expert clinicians (for example, affiliated with a particular locale where a protocol is to be implemented) and intensivists. In particular, when reviewing this information (literature, guidelines, expert knowledge, etc.), in one embodiment, this information may be analyzed to determine various processes, where these processes comprise a set of linked or otherwise related steps involved in that aspect of care.

After a review of the information pertaining to the identified aspect of care, the current state of the aspect of care may be assessed at step 230. The assessment of the aspect of care may involve determining a setting or locale where the aspect of care is administered and the associated availability of resources (for example, the ICU, the operating room (OR), the emergency room (ER), during transport of a patient, some combination, etc.), the duration over which the aspect of care is administered (an hour, week, month, etc.) and the complexity of the current state of the aspect of care, such as the initial criteria associated with the implementation of that aspect of care, the number and types of interventions associated with that aspect of care, the number of variables involved in determining whether to administer an intervention, how many measurements are required to determined if an intervention should be implemented and how often these measurements are required, how many interventions are required and in what time period, etc.

For example, with respect to the current state of the aspect of care of sepsis diagnosis and management it may be determined that the criteria for implementation of that aspect of care comprises numeric thresholds for one or more of temperature (T), heart rate (HR), respiration rate (RR), blood pressure (BP), white blood cell count (WBC), or a subjective assessment of a patient based upon the presence of infection. The setting for sepsis diagnosis and management is an ICU or other full resource setting, an ER, during transport, or some combination, while the duration may be between 1 day and 1 week as the typical ICU length of stay (LOS) is less than one month. The complexity of the current standard of care is that usually 3-5 interventions are required and 5-10 variables are associated with those interventions. The assessment may also involve the association of various processes or interventions with setting or duration or complexity. For example, processes may be correlated with the setting in which they are implemented or the duration over which they are implemented.

In conjunction with assessing the aspect of care, as described above, therapeutic interventions associated with current state of the aspect of care may be identified at step 240. The identification of therapeutic interventions may entail prioritizing the set of therapeutic interventions that comprise at a least a portion of the current state of the aspect of care and determining dose rates, iterative doses, any incremental escalation or an empiric dose related to one or more of the therapeutic interventions.

For example, in the case of sepsis diagnosis and management, therapeutic interventions may include IV fluid delivery, antibiotic administration, blood component therapy, vasopressor therapy, inotrope therapy, activated protein C therapy, etc. where the therapeutic interventions are prioritized according to the best available evidence (such as efficacy statistics or the like) as therapeutic interventions including: IV fluid, antibiotics, blood, vasopressor, inotrope, activated protein C which are prioritized according to best evidence as: IV fluid, antibiotic, vasopressor (increased risk, need invasive monitor); inotrope (increased risk, need invasive monitor); activated protein C (increased risk of hemorrhage). The dosage determined for the above are: IV fluids: empiric dosing; and initial, repeated dose to a mean arterial pressure (MAP) or central venous pressure (CVP) threshold; antibiotic: empiric dose regimen (depending on suspected infection source);

vasopressor: incremental dose (MAP threshold); inotrope: incremental dose; activated protein C: empiric (prioritize with expert clinician opinion).

The variables associated with the aspect of care and the determined interventions may be identified at step 250. This identification process may entail the identification of a set of variables whose values can identify a need for the aspect of care. Additionally, any variables which may be affected by each intervention, including variable derangements associated with a poor outcome for an intervention, (for example, blood glucose concentration greater than 150 mg/dl, etc.), measurement techniques for each variable and the character of each technique (for example, invasive, non-invasive, continuous, periodic or random, ease of measurement or repetition, etc.) and the character of a measurement result (numeric, binary, subjective, etc.) and turn-around time to obtain a result.

In one embodiment, as pertinent to the aspect of care of sepsis diagnosis and management a variable set that identifies need for aspect of care (for example, criteria for diagnosis of sepsis) including BP, HR, RR, T, WBC and a suspected source of infection. Variables affected by each intervention including blood creatinine concentration increase in the previous 24 hour period compared with the current value may be used to identify renal failure, and need for more intensive monitoring or therapy. Measurement technique(s) for each variable may be identified and used to qualify variable and measurement technique for use during protocol (for example, turnaround time is less than the maximum time after intervention to obtain accurate measurement of effect of intervention). These measurement techniques can then be characterized, for example, BP at 5 or 15 minute intervals may be non-invasive and adequately accurate for hemodynamically stable patient, but invasive arterial cannula and continuous real time monitoring may be required for monitoring status during shock and therapy). Whether a technique is continuous, periodic or random: may be determined by assessing the time needed to keep a measurement 'clinically current' and such criteria (for example, 2 minute limit for MAP, 4 hour limit for [lactate], etc.) are required for protocol function. Ease of measurement and need for repetition may be used to determine logic sequence for measurement—intervention—re-measurement and such measurement results will be characterized (for example, as numeric, binary or subjective, etc.).

The therapeutic interventions identified may be further characterized at step 260. This may entail a determination of whether the therapeutic intervention is generally required for the aspect of care, a rating of the importance of the timing of the intervention, a rating of the risk/benefit of the intervention, the complexity of implementing the intervention at the bedside, if the intervention can be implemented as a clinically independent iteration and if a constant support process is needed or available for such an intervention.

For example, in an embodiment of protocol generation where the aspect of care is sepsis diagnosis and management the following interventions may be determined to be required for sepsis mgt: IV fluid (lactated Ringer's solution, LR), antibiotic (local regimen, pharmacy), vasopressor (norepinephrine or other agent), inotrope (dobutamine or other agent), drotrecogin alpha (activated protein C; Xigris, Eli Lilly Corp). The importance of the timing of the various interventions may be IV fluid (volume determined by empiric considerations based on patient's estimated weight), antibiotic (optimally, to be administered within the first hour after start of protocol); vasopressor (possibly required within first hour after start of protocol, possibly ongoing at time of sepsis diagnosis and start of protocol). The risk—benefit analysis for the interventions may be IV fluid (low risk); vasopressor/inotrope (intermediate risk); blood component therapy (packed red blood cell, PRBC, intermediate risk; fresh frozen plasma, FFP, low risk); Xigris (expensive, last resort, risk of hemorrhage).

Based upon the interventions identified for the aspect of care, including identified therapeutic interventions and the corresponding priority and characteristics, a sequence for the therapeutic interventions may be determined at step 270. In one embodiment, this sequence may be determined based on the rating of the time criticality of each of the therapeutic interventions, the rating of the risk of each/benefit of each of the therapeutic interventions and the ability to measure the effectiveness of a therapeutic intervention.

In one embodiment, to devise a master routine to direct therapeutic interventions in a sequence for a sepsis diagnosis and management protocol: it was determined that there was a difference between hemodynamic stability (where, for example, hemodynamic stability is defined as: MAP>=65, HR<120, UO>=0.5) and severe sepsis (aka shock) and that the protocol should be segmented accordingly, with a set of rules applicable to stability and a set of rules applicable to severe sepsis with rules applicable to transition between the two segments. If a patient was stable (explicit immediate determination), then rules which monitor and maintain stability using minimal invasiveness would be used and periodic measurements and threshold as systemic indicator of hemodynamic stability and perfusion adequacy with hourly or more frequent re-check of ongoing hemodynamic stability with key variable set. A cumulative IV fluid volume threshold for transition to the severe sepsis segment was determined along with a hemodynamic instability threshold for transition to the severe sepsis segment and checks for organ dysfunction or failure thresholds for transition to the severe sepsis segment.

In general it was determined that in the severe sepsis segment would be an explicitly time limited sepsis management protocol, (for example, 24 hours) based on a determination (critically unstable; explicit immediate determination, for example based on thresholds)) where the rules would entail more invasive monitoring and more intensive therapy set such as fluid/blood or vasopressor/inotrope therapy, as needed by the individual patient with a reduction or gradual curtailment of such vasopressor therapy if possible.

The sequence of therapeutic interventions may be used, at step 280, to devise a master routine to direct therapeutic interventions in sequence. This sequencing may, in one embodiment, entail a comparison of thresholds associated with each intervention, where therapeutic interventions can be sequenced based upon the thresholds (for example, if one set of thresholds is less than another the therapeutic intervention associated with the first set of thresholds may be sequenced before the other therapeutic intervention). The sequencing may also entail a determination of time intervals between one or more measurements and the implementation of an intervention, or a re-check of a measurement. Additionally, such a sequence may be based on the feasibility of implementing simultaneous interventions and the coordination of therapeutic interventions.

Once the sequence of therapeutic interventions is determined iterative logic for each therapeutic intervention can be devised at step 290. Devising this iterative logic may entail forming rules to iterate a therapeutic intervention or when to proceed to another therapeutic intervention in the sequence. Such rules may be associated with measurements of an intervention specific variable for threshold comparison, such that if the threshold(s) is exceeded, then an intervention request (for example, for the intervention) is made and the quantity and rate of intervention is determined. If the threshold is not exceeded, then a time interval for a recheck may be determined. A time interval for recheck after the completion of the intervention may also be determined. If the physiologic variable threshold measurement—therapeutic intervention—recheck threshold process is clinically independent, then this process can be described as an independent algorithm (which may be utilized as an independent segment), with call from and return to the master routine may be added.

In one embodiment applicable to a protocol for sepsis diagnosis and management, devising an iteration subroutine for each therapeutic intervention comprises determination of logic for fluid and blood therapy; vasopressor therapy, including explicit logic for increment of continuous support therapy to obtain specific variable effect (for example, MAP>=65) and complementary logic to attempt decrease/stop of vasopressor therapy; inotrope therapy, including explicit logic for increment of continuous support therapy to obtain specific variable effect (for example, systemic oxygenation, measured as systemic hemoglobin oxygen saturation>70%) or, alternatively, explicit logic to direct a more intensive monitor of hemodynamic function, for example pulmonary artery catheter (PAC) directed therapy.

At this point, then, a protocol for use with the aspect of care may have been developed, where the protocol comprises a number of rules operable to implement a set of sequenced therapeutic interventions and logic to select between the rules based upon thresholds associated with various measurement. One outgrowth of the application of embodiments of such a methodology to the development of protocols for aspects of care is that the resulting protocols may be segmented according to severity, clinical independence of a particular therapy process, or based on a number of other criteria.

Specifically, the segmentation of a protocol may comprise the grouping of the rules into segments which can be substantially independently utilized by a clinician, but which may be applied in tandem to address an aspect of care. The segmentation of the protocol may be based on a number of different criteria, including the invasiveness of monitoring or of therapeutic intervention involved with the implementation of the rules of the segments (for example, more invasiveness involved with obtaining measurements or administration of medication, etc.), the severity of the application of the rules of the segment on a patient including risk to the patient or the effects of medication to be administered in conjunction with the segment, the ability to administer or perform the rules of a segment in a separate clinical setting or in conjunction with other protocols, or any of a number of other criteria which may result in the grouping of rules into segments when forming the protocol.

It may be useful to illustrate a particular protocol which resulted from the application of the above methodology for generating a protocol, where the protocol is segmented according to one or more criteria. Accordingly, attention is now directed to FIGS. 3-8 which illustrate one embodiment of a protocol for the diagnosis and management of sepsis. The protocol may comprise a number of rules which have been segmented according to various criteria. It may be useful before delving into the specific segments and rules of the protocol to give a general overview of the segmentation of the protocol.

Figure 3B:
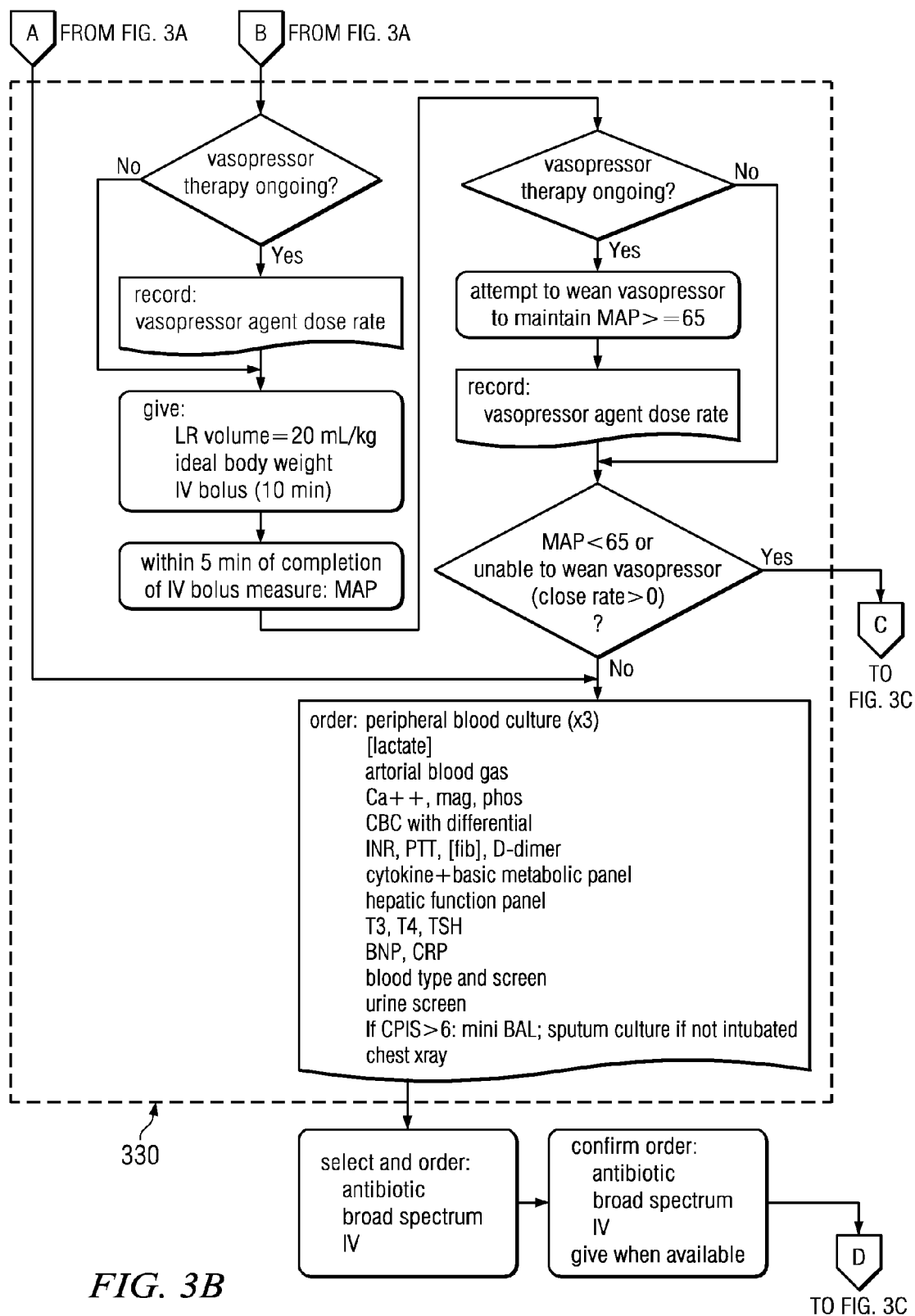
FIG. 3 is a flow diagram representing one embodiment of the rules of a segment of a protocol for sepsis diagnosis and management.
Figure 3C:
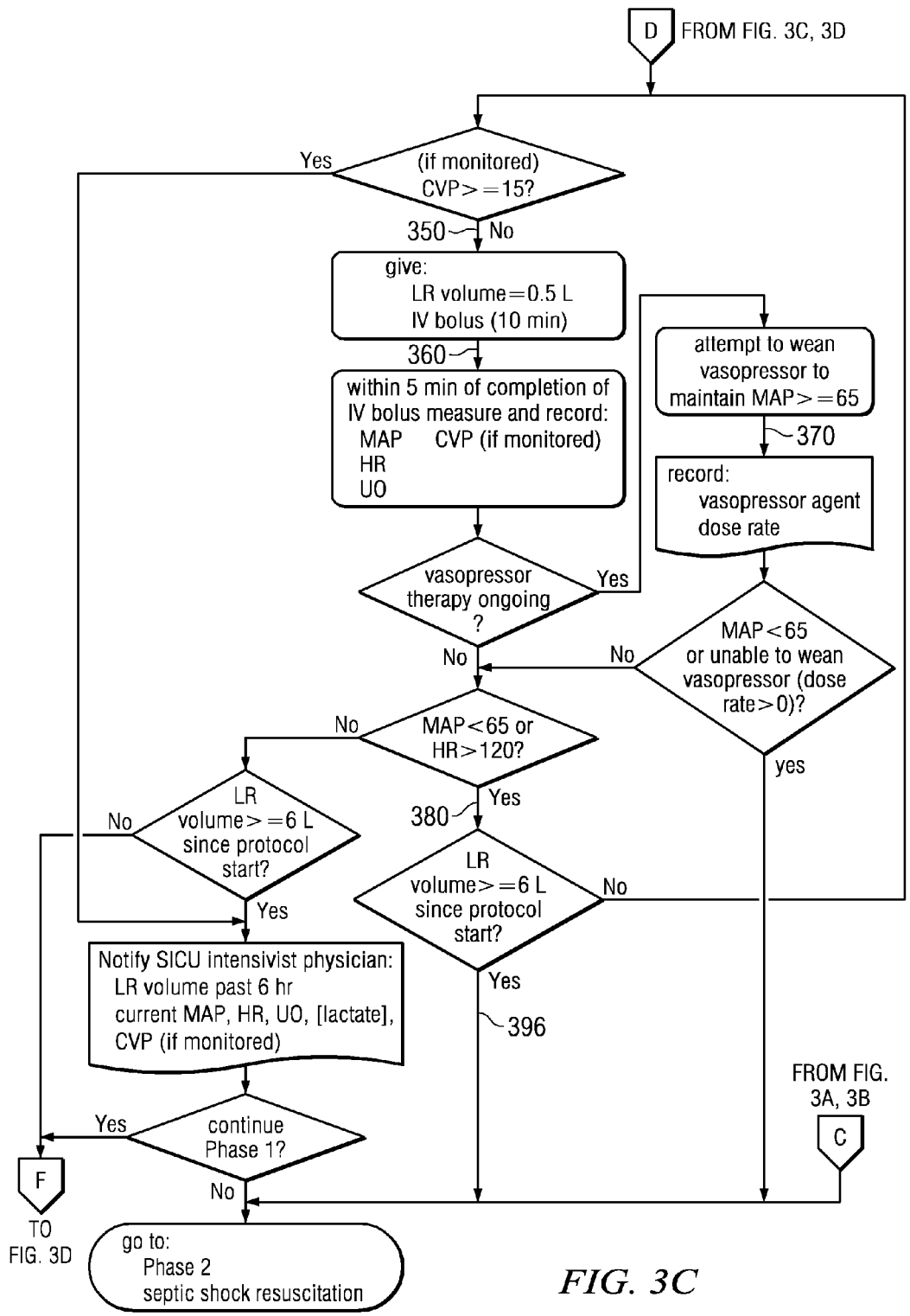
Figure 3D:
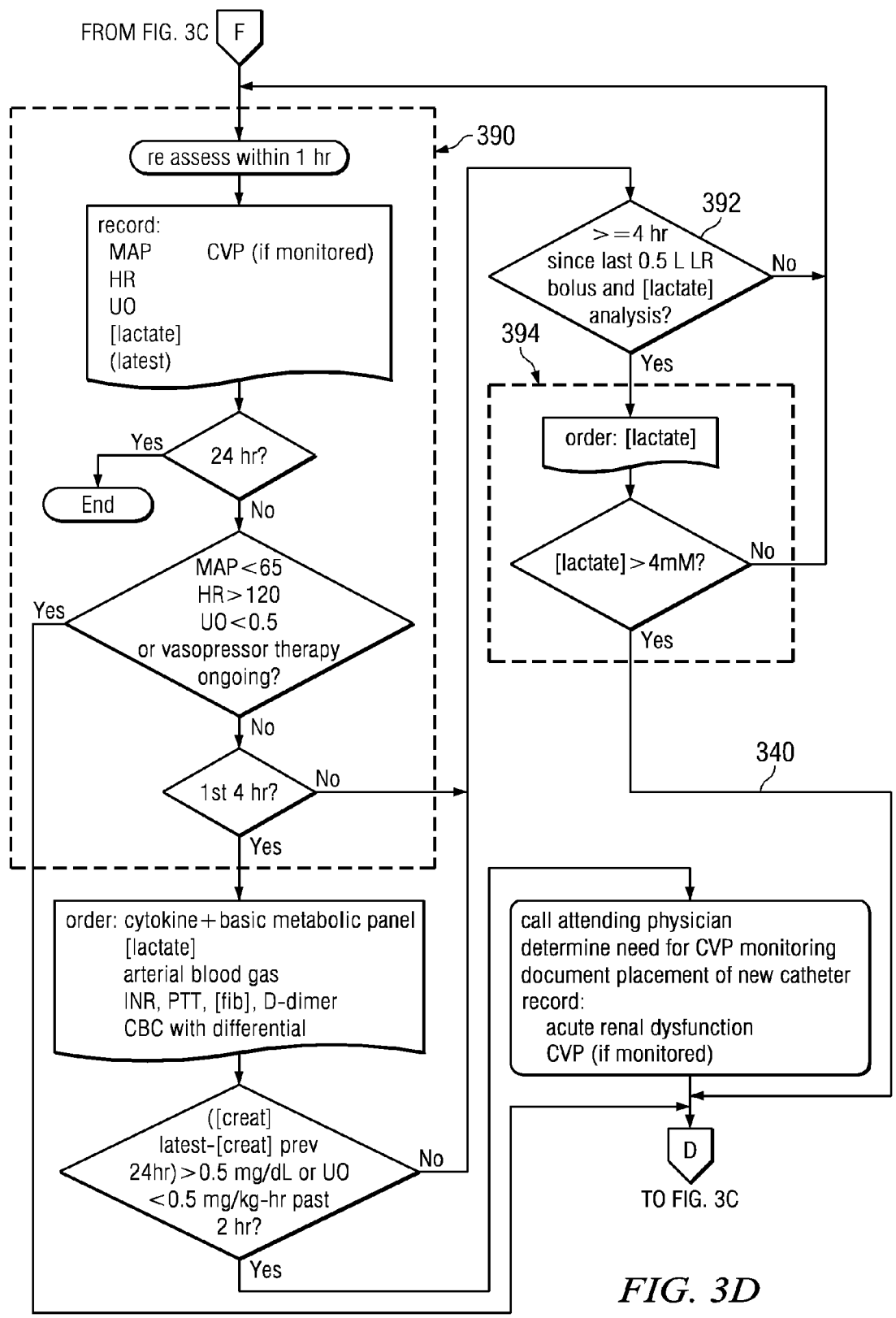
Figure 4B:
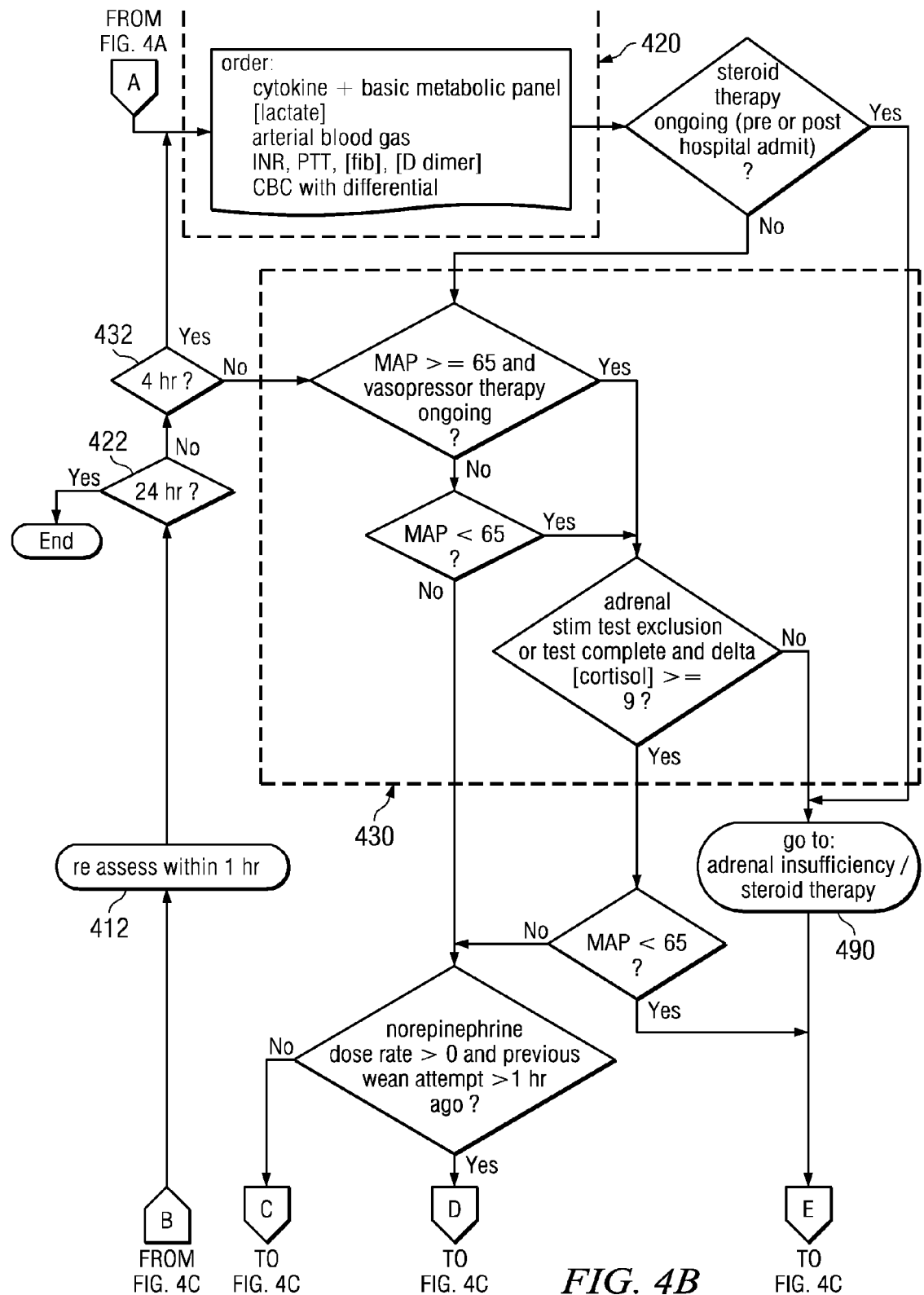
FIG. 4 is a flow diagram representing one embodiment of the rules of a segment of a protocol for sepsis diagnosis and management.
Figure 4C:
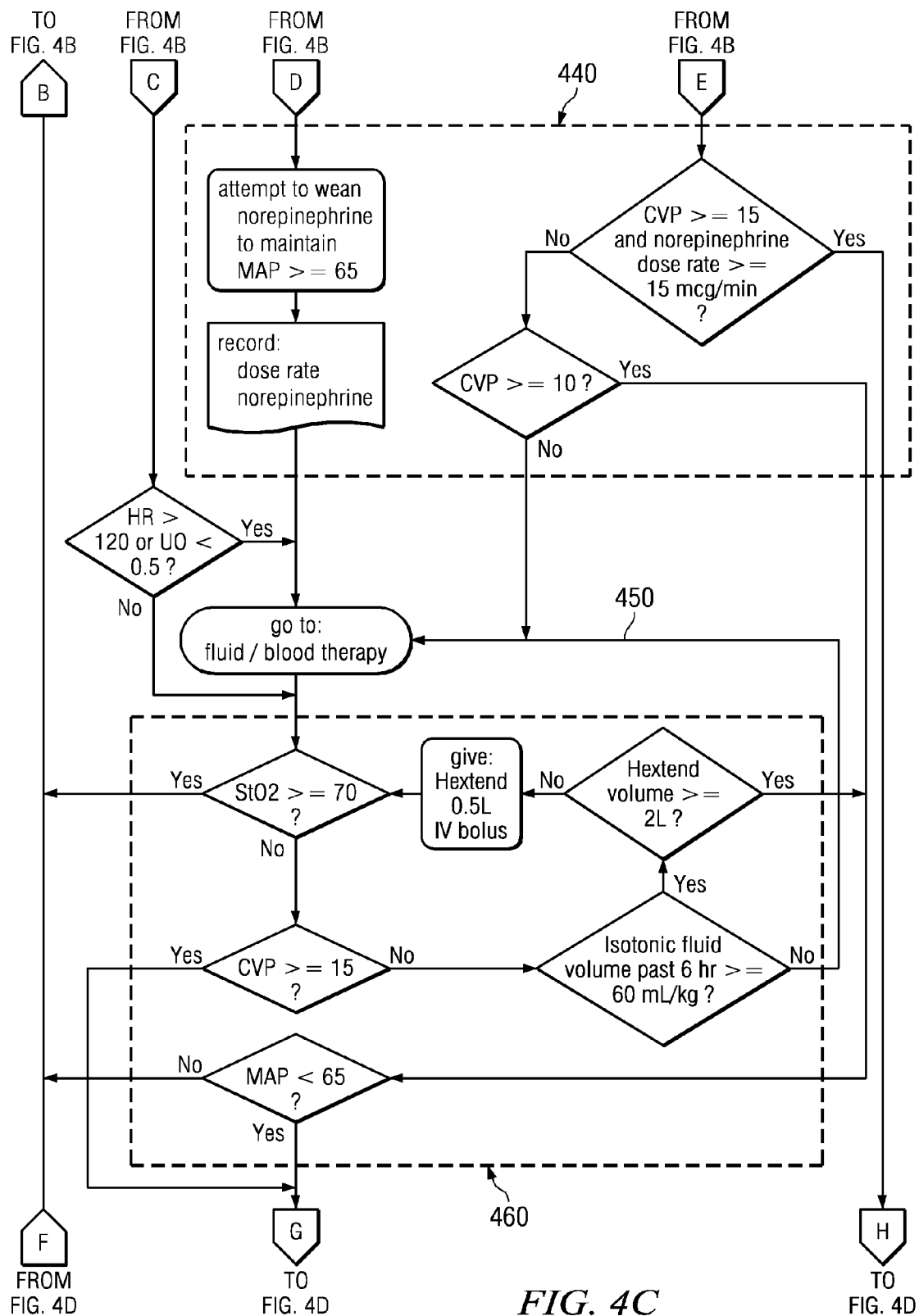
Figure 4D:
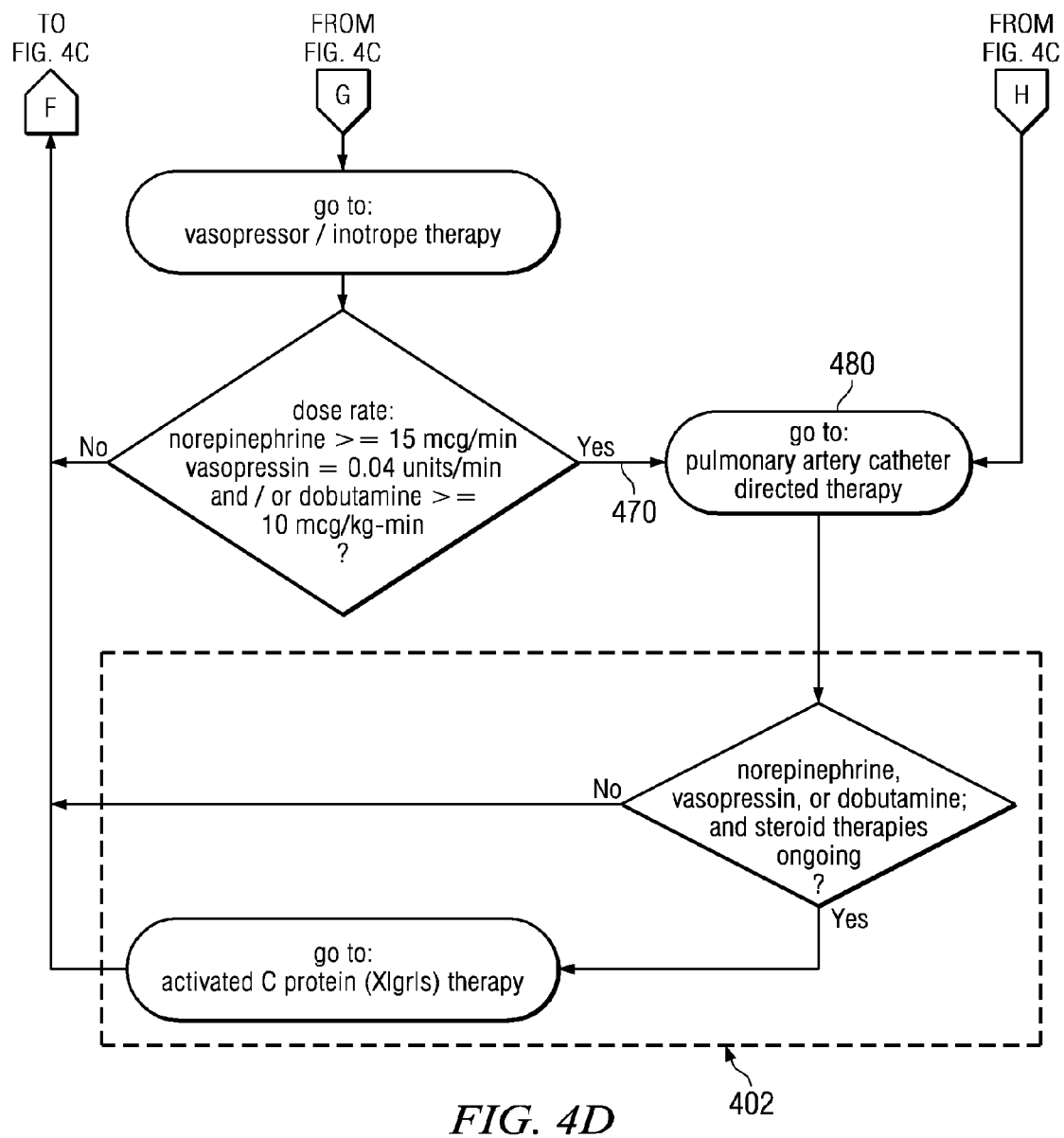

In the embodiment illustrated, FIGS. 3 and 4 illustrate segments of the embodiment of the protocol for the diagnosis and management of sepsis where the rules comprising these various segments have been grouped according to severity of diagnosis and invasiveness of application of the rules. Generally, then, the segment of FIG. 3 represents rules for the diagnosis and management of sepsis which are applicable to relatively less severe sepsis (also referred to as sepsis), wherein the rules may be applied (for example, measurements taken, medications delivered, etc.) relatively less invasively and with commensurately less risk to the patient. In contrast, FIGS. 4-8 represent a segment of the protocol for the diagnosis and management of relatively more severe sepsis including septic shock (collectively referred to herein as severe sepsis) where the application of the rules of this segment are addressed to more severe sepsis and the application of these rules entail invasive methods of monitoring the patient or delivery of drugs with intensive physiologic effects, the administration of drugs with potential side effects, etc. (for example, using a pulmonary artery catheter, the use of a central venous catheter, the administration of vasopressor or inotrope drugs, etc.).

Furthermore, it may be the case that certain segments of the protocol may be further segmented based on certain criteria. Here, FIGS. 5-8 further represent embodiments of segments of the protocol where the rules have been grouped into segments based on the ability to clinically separate the administration of the rules comprising the segment, or the rules are separated based on their applicability to a specific area, medication, measurement, etc.

Figure 5A:
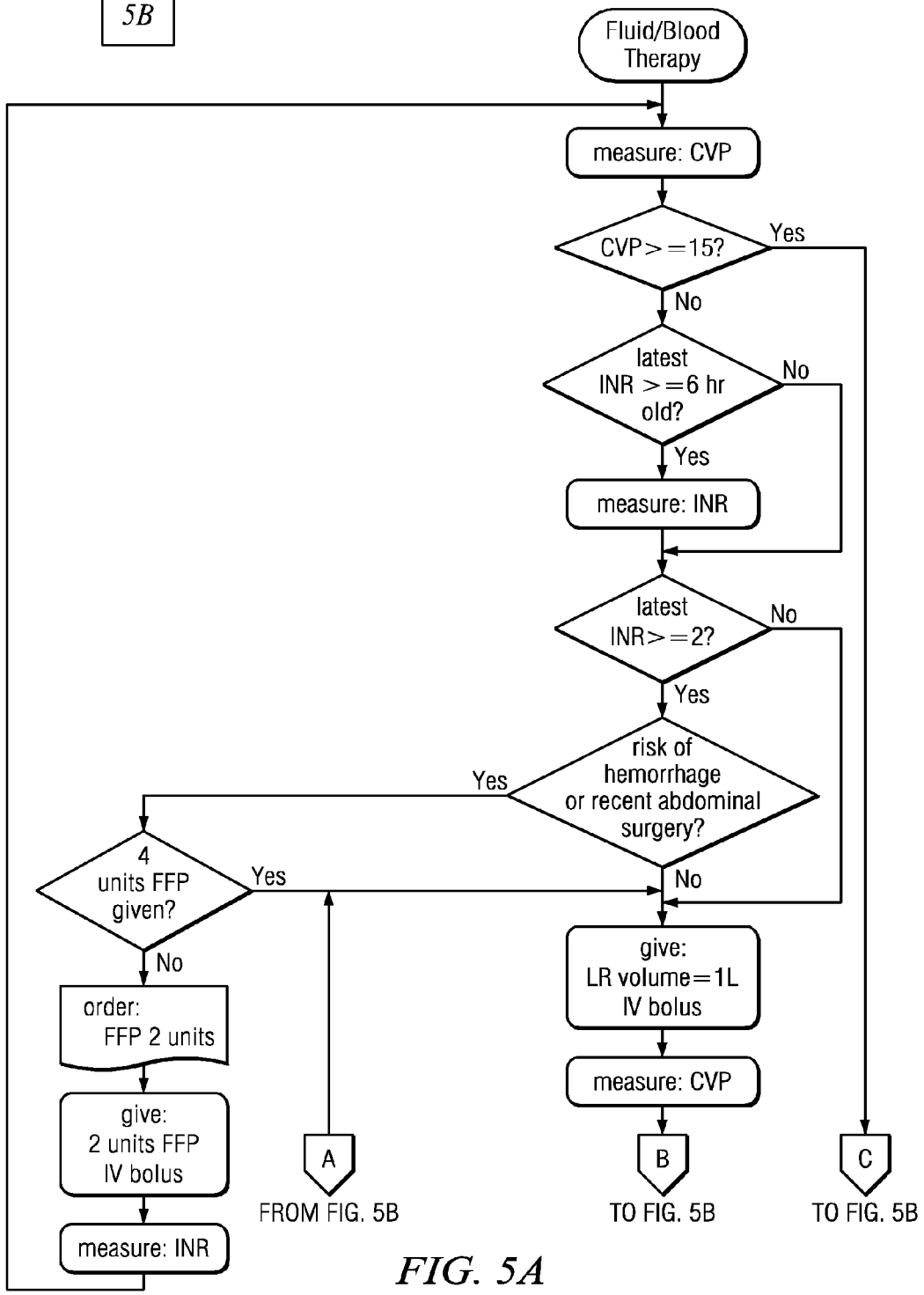
FIG. 5 is a flow diagram representing one embodiment of the rules of a segment of a protocol for sepsis diagnosis and management.
Figure 5B:
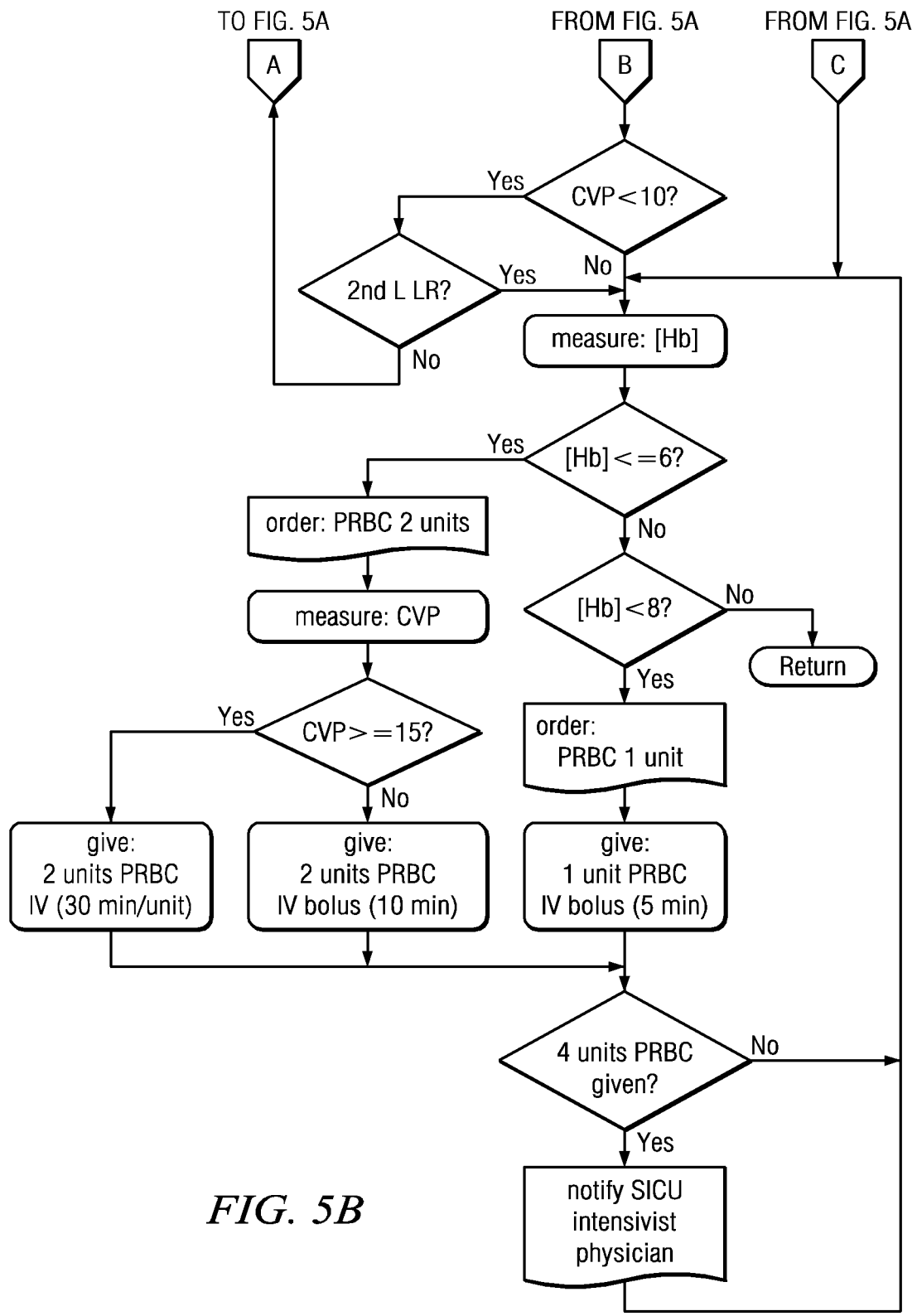
Figure 6A:
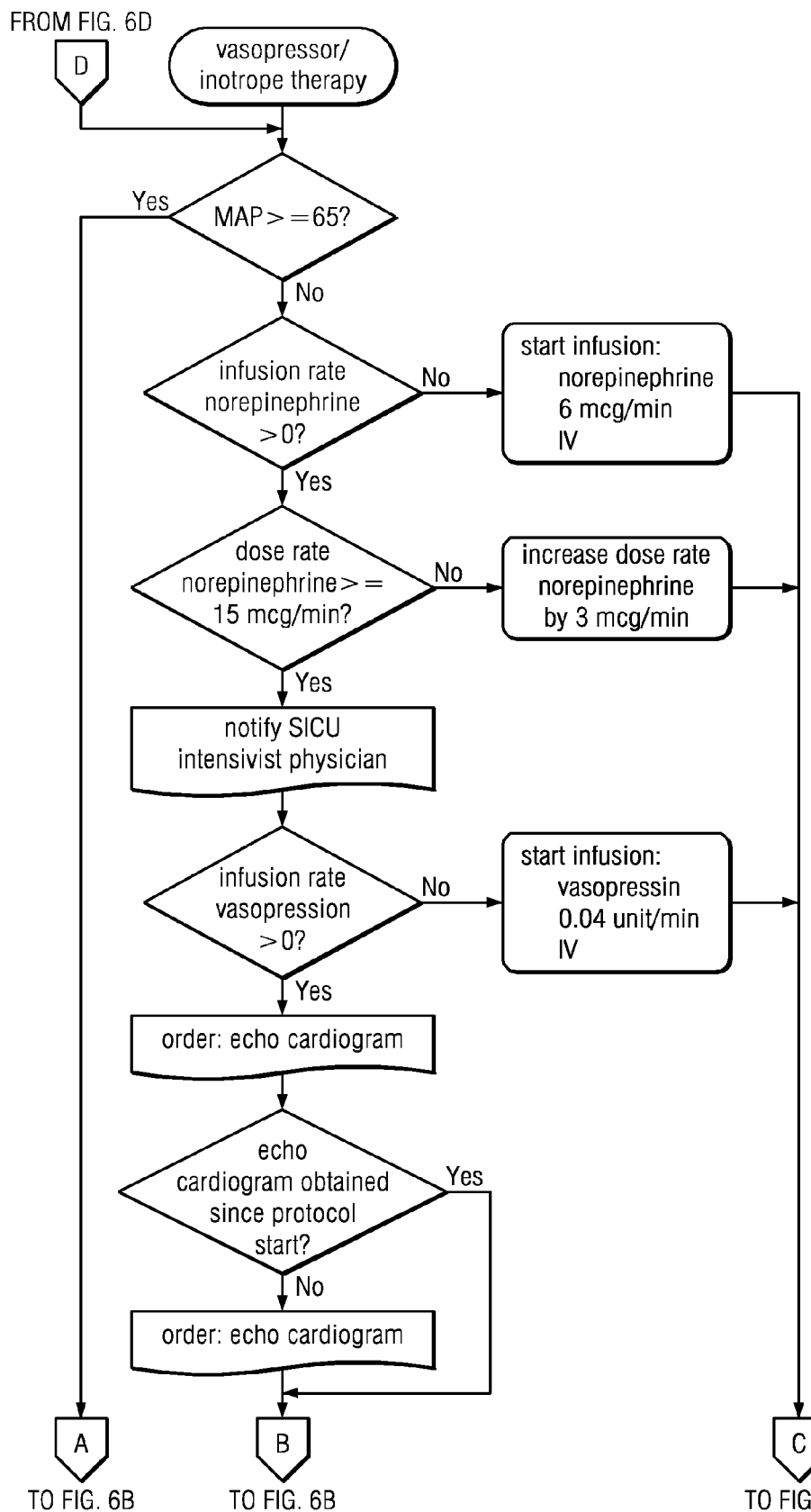
FIG. 6 is a flow diagram representing one embodiment of the rules of a segment of a protocol for sepsis diagnosis and management.
Figure 6B:
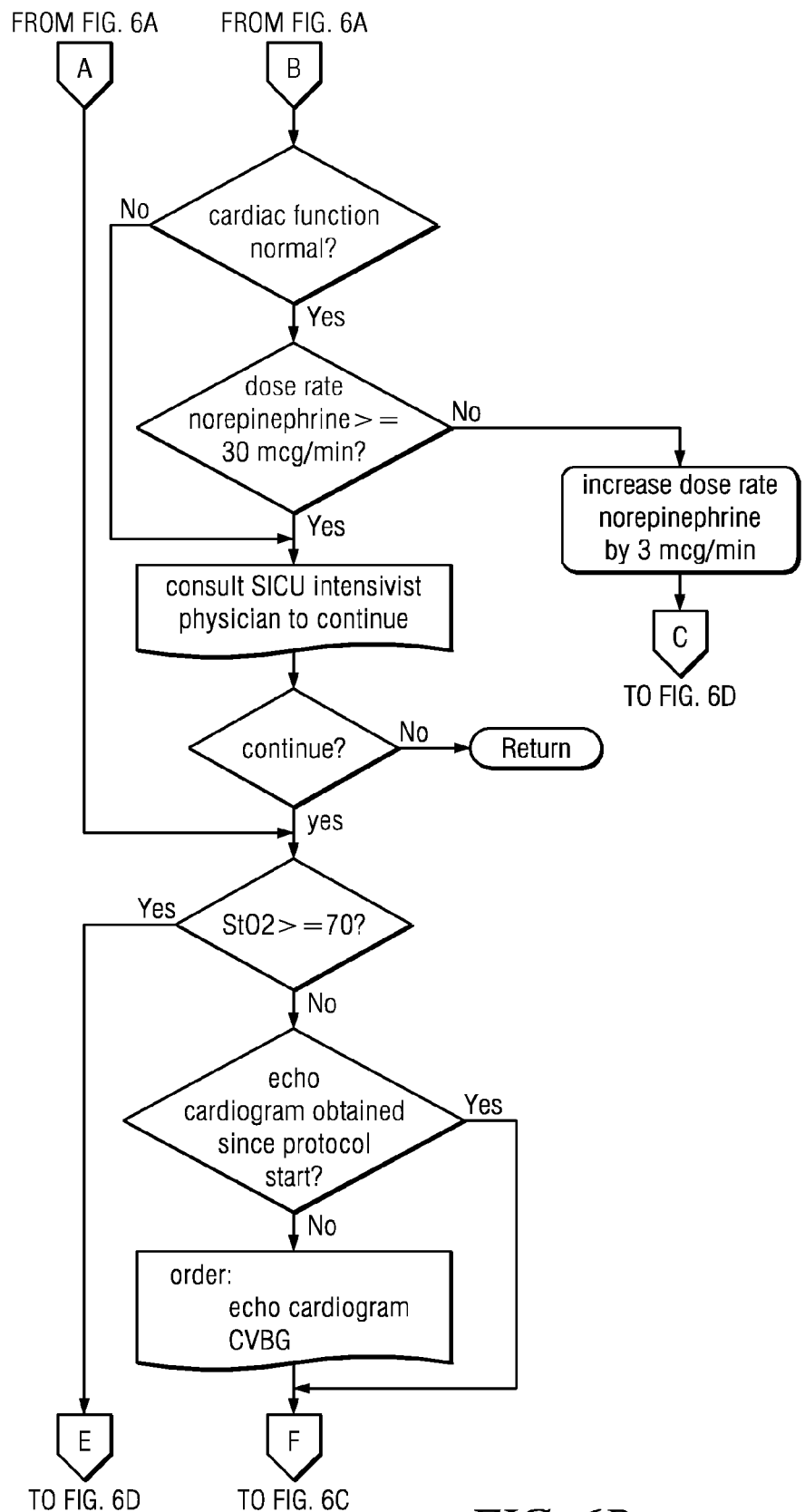
Figure 6C:
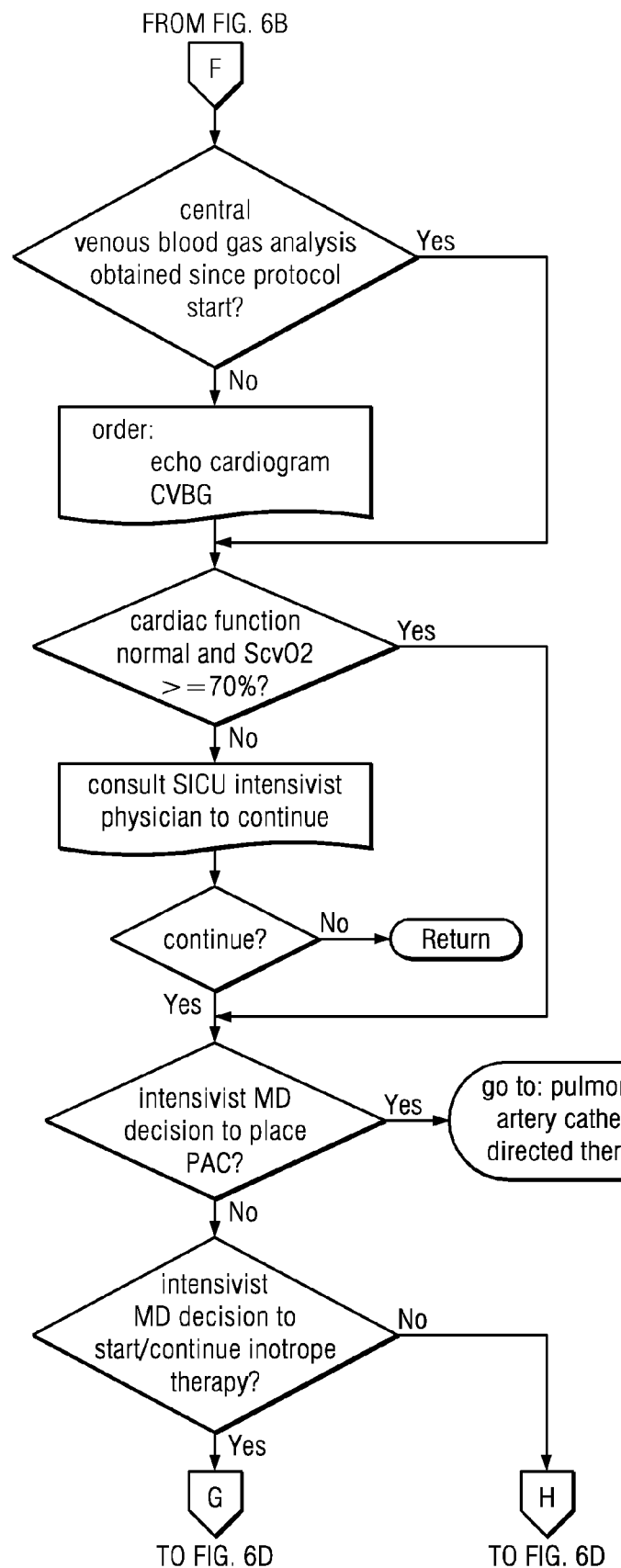
Figure 6D:
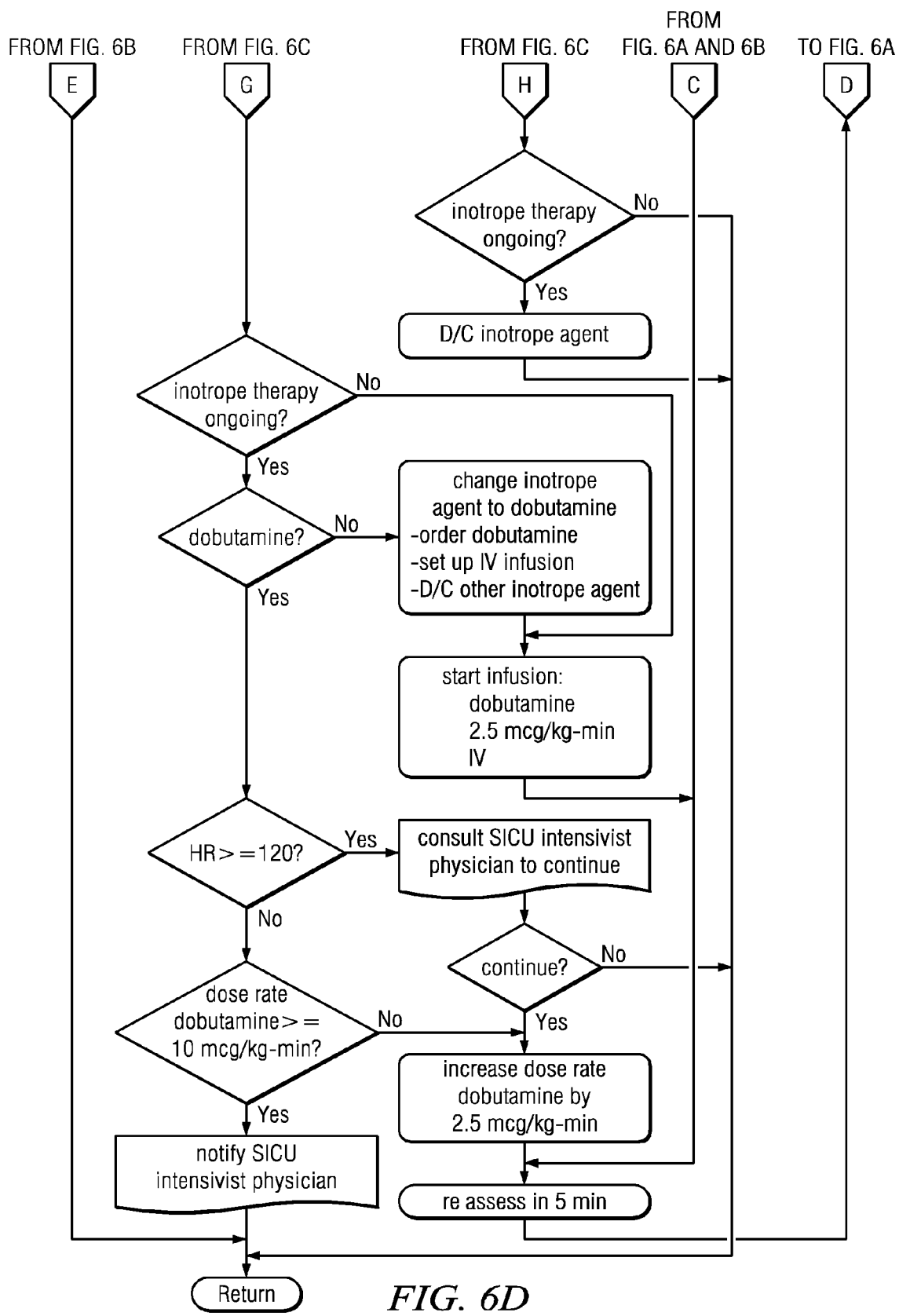
Figure 7A:
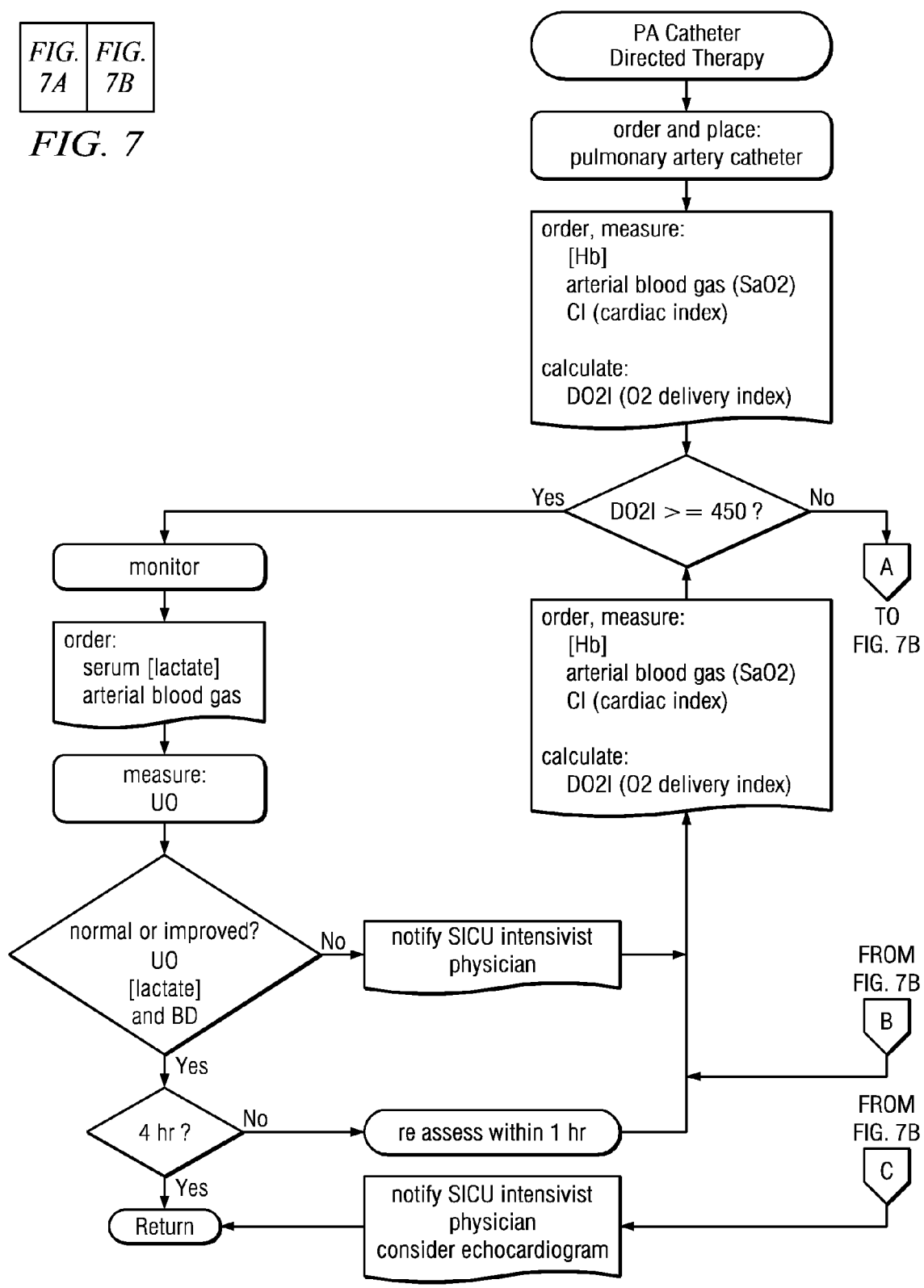
FIG. 7 is a flow diagram representing one embodiment of the rules of a segment of a protocol for sepsis diagnosis and management.
Figure 7B:
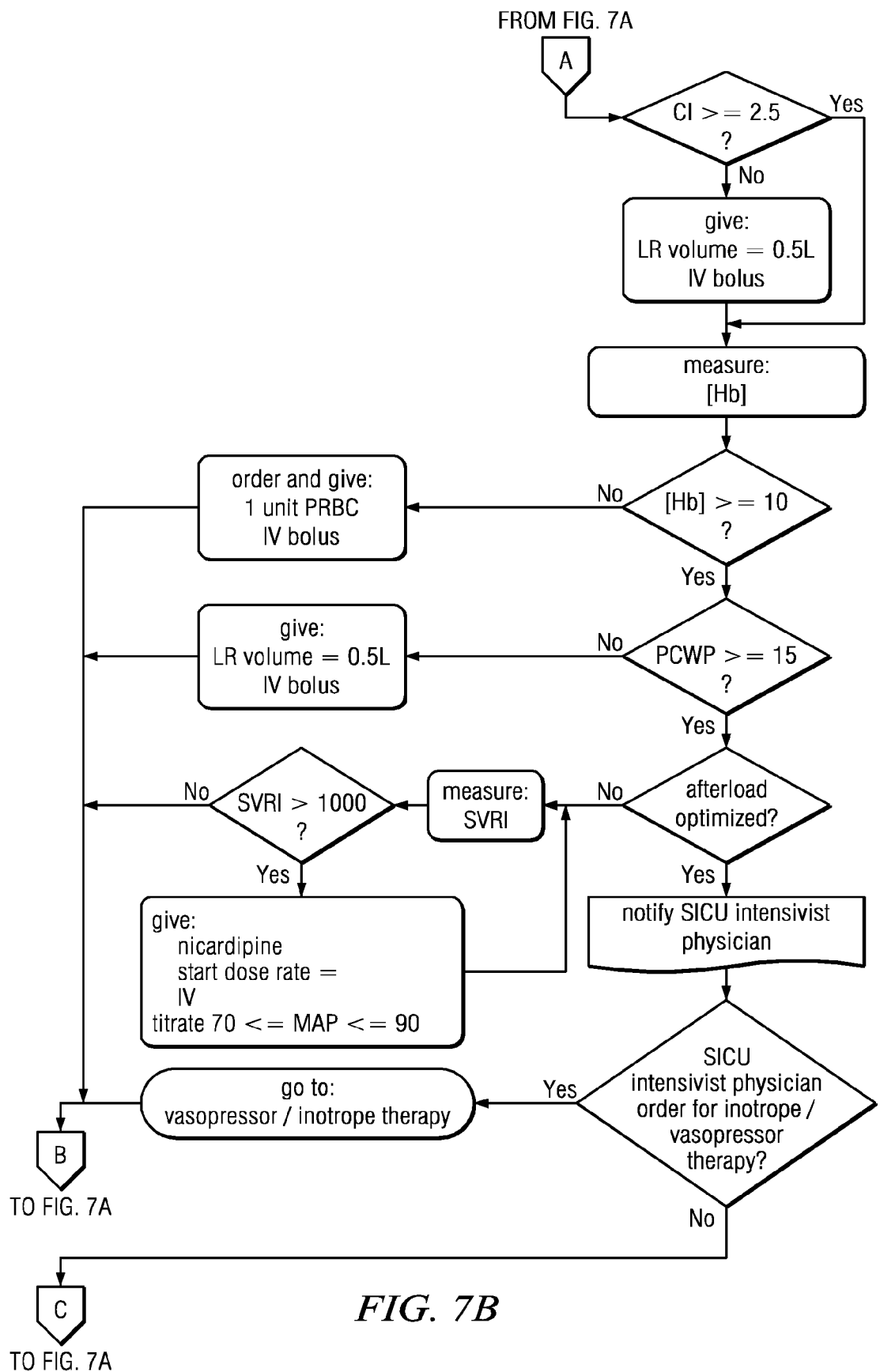
Figure 8:
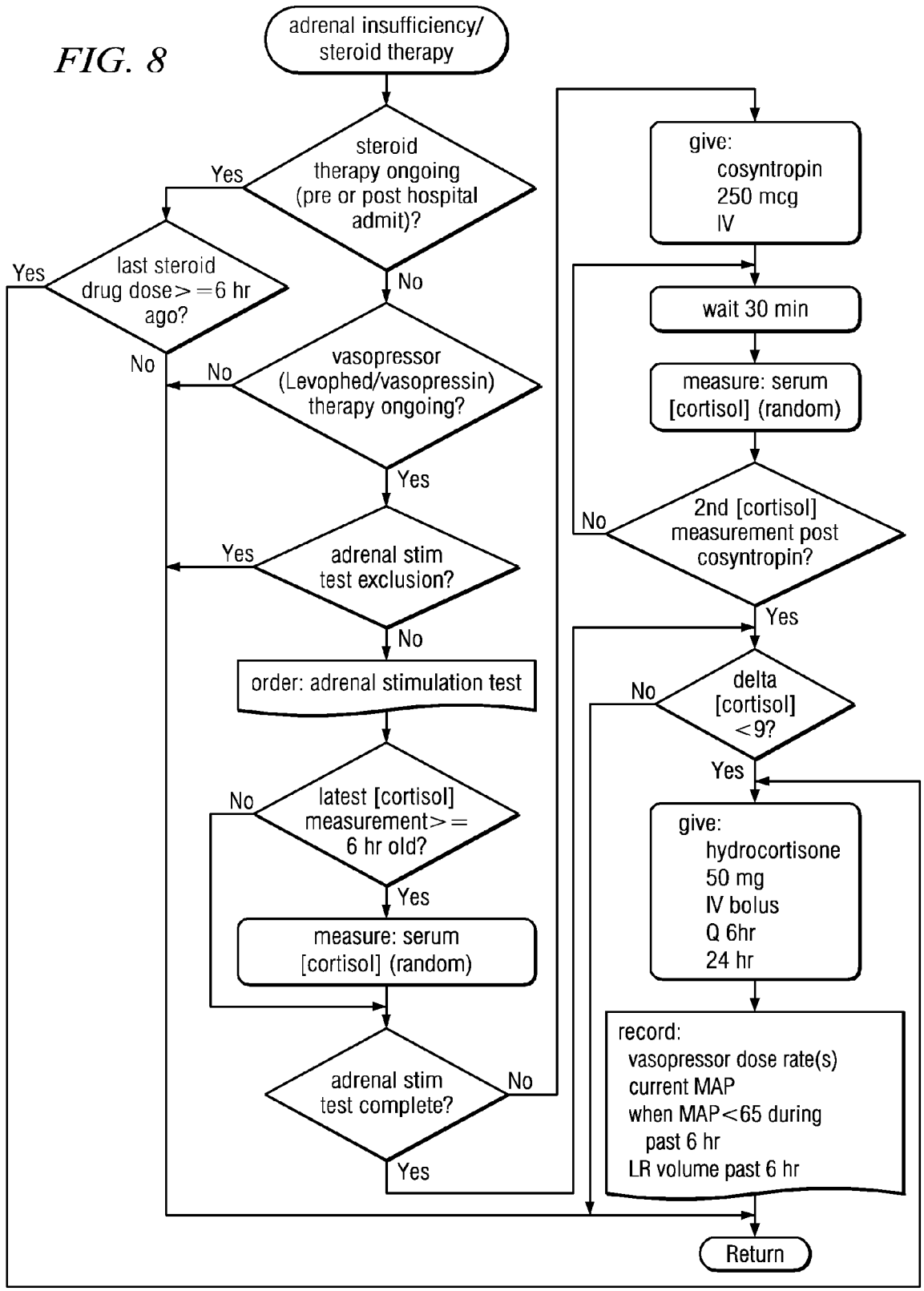
FIG. 8 is a flow diagram representing one embodiment of the rules of a segment of a protocol for sepsis diagnosis and management.

In this embodiment then, FIG. 5 is represents one embodiment of a segment of the protocol for sepsis diagnosis and management where rules of the segment have been grouped according to fluid/blood therapy. As can be seen then, rules comprised by the fluid/blood therapy segment may also be considered to be comprised by the grouping of rules according to sever sepsis or septic shock. This may also be the case with the rules of the segments depicted in FIGS. 6-8 as well. Moving on to FIG. 6, one embodiment of a segment of the protocol for sepsis diagnosis and management where rules of the segment have been grouped according to vasopressor/inotrope therapy is depicted. FIG. 7 depicts one embodiment of the protocol for sepsis diagnosis and management where rules of the segment have been grouped according to adrenal insufficiency/steroid therapy and FIG. 8 depicts one embodiment of the protocol for sepsis diagnosis and management where rules of the segment have been grouped according to pulmonary arterial catheter (PAC) directed therapy.

Each of the various segments of the embodiment for a protocol for sepsis diagnosis and management as represented in FIGS. 3-8 may now be discussed in more detail. Turning first to FIG. 3, at step 310 a patient can be assessed for sepsis. This assessment may comprise applying one or more rules configured to implement a point or score based screening where points are based upon measurements of patient condition (referred to herein collectively as scoring), including temperature, heart rate, respiration rate, white blood cell count, etc. Additionally a suspected source of infection may be identified. This scoring system may, for example, generate a score based on if T>38 C or T<36 C, HR>90 bpm, RR>20 bpm or $PaCO_2$<32 mmHg or WBC>12000 or WBC<4000 cells/$mm^3$ and may ask a practitioner to identify a suspected source of infection (for example: line, pneumonia, abdomen, cellulitis/soft tissue, urinary tract, etc.) FIGS. 9A and 9B depicts one embodiment of a sheet which may be utilized by a clinician (such as nurse practitioner or the like) to complete a sepsis screening process.

Returning to FIG. 3, at step 310 if the criteria for a diagnosis of sepsis are met, at step 320 vital signs are recorded, recent lab data reviewed, IV access established and a urine output monitor utilized. More specifically in one embodiment the following actions are taken: record body core temperature (T), heart rate (HR), respiratory rate (RR), mean arterial pressure (MAP), urine output rate (UO), partial pressure of carbon dioxide in arterial blood (PaCO2), white blood cell count (WBC), blood lactate concentration ([lactate]), Glasgow Coma Scale (GCS) score and suspected source of infection. If catheters are not present, then place: peripheral IV catheter (18 gauge), peripheral IV catheter (20 gauge), foley catheter (with T sensor) and document catheter placement procedures in chart. Determine need for new or existing central venous catheter. If new central venous catheter is required, then document placement in chart and document reason as: congestive heart failure (CHF), pulmonary hypertension or inadequate peripheral IV access. If required, then measure central venous pressure (CVP). If CVP≧15 mmHg, then notify intensivist physician, and, based on information including current MAP, HR, UO, [lactate], and CVP, decide whether to continue the first segment of the protocol (one embodiment depicted in FIG. 3) or start the second segment of the protocol (one embodiment depicted in FIG. 4). This determination may include assessing for septic shock, including assessing the suspected source of infection and assessing hypotension (MAP<65 mmHg (measured and recorded) or MAP≧65 mmHg and vasopressor therapy ongoing).

At step 330 a diagnosis of septic shock may be confirmed. More specifically in one embodiment the following actions are taken: determine hypotension (MAP<65 mmHg) or normotension (MAP≧65 mmHg) with vasopressor therapy ongoing (for example, post operation prior to ICU admit). If normotension (MAP≧65 mmHg) with vasopressor therapy ongoing, then record vasopressor agent and vasopressor agent dose rate. If hypotension (MAP<65 mmHg) or normotension (MAP≧65 mmHg) with vasopressor therapy ongoing, then give Lactated Ringer's (LR) fluid: 20 mL/kg, ideal body weight; IV bolus (use pressure bag). Measure MAP within 5 minutes of completion of 20 mL/kg IV fluid bolus. If vasopressor therapy is ongoing, then attempt to wean vasopressor to maintain MAP≧65 mmHg. Record vasopressor agent and vasopressor agent dose rate. If vasopressor therapy is not ongoing, then determine if hypotension (MAP<65 mmHg) persists after fluid administration. If MAP<65 or unable to wean vasopressor (patient is unresponsive to fluid and septic shock is ongoing) then go to step 396.

Otherwise, at step 340 antibiotic therapy is started after record a suspected or confirmed microorganism. More specifically in one embodiment the following actions are taken: select correct antibiotic agent from table below.

| Antibiotic drug | if severe Vancomycin allergy, then substitute Linezolid | Regimen 600 mg q12 hr |
|---|---|---|
| Indication | 1. 1st line<br>2. 2nd line | $^a$monitor, adjust for renal dysfxn<br>$^b$for severe β lactam allergies; kinetic monitoring |
| Pneumonia | | |
| Community acquired | 1. Ceftriaxone +<br>Azithromycin<br>2. Levofloxacin | 1 g IV q24 h<br>500 mg IV/PO q24 h<br>$^a$750 mg IV q24 h |
| Community aspiration | Add Clindamycin or change Ceftriaxone to Piperacillin/Tazobactam | 600 mg IV q8 h<br><br>$^a$4.5 g IV q6 h |
| Ventilator associated | | |
| early (<5 dy) | 1. Cefepime<br>2. Ciprofloxacin | $^a$2 g IV q12 h<br>$^a$400 mg IV q12 h |
| late (pseudomonas risk) | 1. Cefepime +<br>Vancomycin +<br>Tobramycin<br>2. Ciprofloxacin +<br>Vancomycin +<br>Clindamycin | $^a$2 g IV q24 h<br>$^a$15 mg/kg IV q12 h<br>$^{a,b}$7 mg/kg IV<br>$^a$400 mg IV q12 h<br>$^a$15 mg/kg IV q12 h<br>900 mg IV q8 h |
| Catheter related | | |
| Urinary catheter; UTI<br>IV, art cath; bloodstream<br>Wound/Soft Tissue | 1. Piperacillin/Tazobactam<br>2. Ciprofloxacin<br>Vancomycin | $^a$4.5 g IV q6 h<br>$^a$400 mg IV q12 h<br>$^a$15 mg/kg IV q12 hr<br>(after cath removal) |
| Necrotizing fasciitis | 1. Piperacillin/Tazobactam +<br>Vancomycin +<br>Clindamycin<br>2. Ciprofloxacin +<br>Vancomycin +<br>Clindamycin | $^a$4.5 g IV q6 h<br>$^a$15 mg/kg IV q12 h<br>900 mg IV q8 h<br>$^a$400 mg IV q12 h<br>$^a$15 mg/kg IV q12 h<br>900 mg IV q8 h |
| Surgical site infection | 1. Piperacillin/Tazobactam +<br>Vancomycin<br>2. Ciprofloxacin +<br>Vancomycin | $^a$4.5 g IV q6 h<br>$^a$15mg/kg IV q12h<br>$^a$400 mg IV q12 h<br>$^a$15 mg/kg IV q12 h |
| Intra abdominal | 1. Imipenem/Cilistatin +<br>Vancomycin +/−<br>Fluconazole<br>2. Ciprofloxacin +<br>Metronidazole +<br>Vancomycin +/−<br>Fluconazole | $^a$500 mg IV q6 h<br>$^a$15 mg/kg IV q12 h<br>$^a$800 mg IV q24 h<br>$^a$400 mg IV q12 h<br>500 mg IV q8 h<br>$^a$15 mg/kg IV q12 h<br>$^a$800 mg IV q24 h |

As soon as available, give selected antibiotic agent using prescribed dose rate and schedule.

At step 350 give Lactated Ringer's (LR) fluid: 0.5 L; IV bolus (use pressure bag) and at step 360 Measure and record MAP, HR, UO, and (if monitored) CVP within 5 min of completion of IV fluid bolus.

Following this, at step 370 it can be determined if vasopressor therapy is ongoing. If vasopressor therapy is ongoing, then attempt to wean vasopressor to maintain MAP 65 mmHg. Then record vasopressor agent and vasopressor agent dose rate. If MAP<65 mmHg or unable to wean vasopressor, i.e. patient is unresponsive to fluid therapy, requires vasopressor therapy, and septic shock is ongoing, then go to step 396. If MAP≧65 mmHg and able to wean vasopressor, i.e. patient is responsive to fluid therapy, does not require ongoing vasopressor therapy, then go to step 380.

At step 380 if vasopressor therapy is not ongoing, then determine if hypotension (MAP<65 mmHg) or tachycardia (HR>120 beats per minute (bpm)) persists after fluid therapy. If MAP<65 mmHg and/or HR>120 bpm, then determine total IV fluid volume given since protocol start. A decision can then be made whether to repeat fluid bolus based and hemodynamic instability can be assessed. More specifically in one embodiment the following actions are taken: If MAP<65 mmHg and/or HR>120 bpm, and if total LR volume≧6 L (i.e. 20 mL/kg fluid challenge IV bolus+0.5 L LR IV boluses, or 12 0.5 L LR IV boluses) has been given in past 6 hr, then go to step 396. If total LR volume<6 L has been given in past 6 hr (for example, total LR volume=20 mL/kg fluid challenge IV bolus+0.5 L LR IV boluses<6 L, or <12 0.5 L LR IV boluses), then go to step 350. Otherwise repeat 0.5 L IV LR fluid bolus, then go to step 360. Re-measure MAP, HR UO, then go to step 370. With respect to hemodynamic stability: If MAP≧65 and HR≦120, then determine total LR volume given. If total LR volume=20 mL/kg fluid challenge IV bolus+0.5 L LR IV boluses<6 L, or if <twelve 0.5 L boluses have been given in past 6 hr, i.e. total LR volume<6 L in past 6 hr, then go to step 390. Reassess hemodynamic stability and renal function within 1 hr. If total LR volume=20 mL/kg fluid challenge IV bolus+0.5 L LR IV boluses≧6 L, or if ≧twelve 0.5 L boluses have been given in past 6 hr, (for example, total LR volume≧6 L in past 6 hr) then notify intensivist physician, and, based on information including LR volume past 6 hr, and current MAP, HR, UO, [lactate], and CVP (if monitored), decide whether to continue the first segment of the protocol (one embodiment depicted in FIG. 3) or start the second segment of the protocol (one embodiment depicted in FIG. 4). If decision to continue with the first segment then go to step 390 reassess hemodynamic stability and renal function within 1 hr. If the decision is made to start the second segment, then go to step 396 at which point the sever sepsis segment of the protocol may be implemented.

At step 390 hemodynamic stability and renal function may be assessed. More specifically in one embodiment the following actions are taken: if MAP<65, HR>120, UO<0.5, and/or vasopressor therapy ongoing, then determine if CVP is being monitored. If CVP is being monitored, then record CVP. If CVP≧15, then notify an intensivist physician, and, based on information including LR volume past 6 hr, and current MAP, HR, UO, [lactate], and CVP (if monitored), decide whether to continue with the first segment of the protocol (one embodiment depicted in FIG. 3) or start the second segment of the protocol (one embodiment depicted in FIG. 4). If CVP<15, then go to step 350 and give another 0.5 L LR IV bolus. If ≧24 hr since start of the protocol, then patient care under the protocol may end, which may entail notifying an intensivist physician and record in the protocol end time and orders to proceed with standard monitoring orders. If UO≧0.5, then go to step 392 Otherwise, determine time since last 0.5 L LR IV bolus. If <4 hr since last 0.5 L LR IV bolus, then determine time since last [lactate] analysis. If ≧4 hr since last [lactate] analysis, then go to step 394.

At step 392 If <4 hr since last 0.5 L LR IV bolus, then determine time since last [lactate] analysis. If hr since last [lactate] analysis, then go to step 394 where if ≧4 hr since last [lactate] analysis, then: order [lactate] analysis. If [lactate]>4 mM, then go to step 350. Otherwise repeat 0.5 L IV LR fluid bolus, then go to 360. Then re-measure MAP, HR UO, then go to 370 and reassess hemodynamically stability.

At step 396 proceed to the segment of the protocol for sepsis diagnosis and management intended for severe sepsis, one embodiment of which is depicted in FIG. 4. At step 410 hemodynamic stability can be assessed and established. If vasopressor administration is ongoing (for example, post op prior to ICU admit), then determine if norepinephrine IV is the agent being administered. If norepinephrine is being administered, and if MAP<55, then: increase norepinephrine (Levophed) dose rate by 5 mcg/min; IV; titrate dose rate to obtain 65≦MAP≦75 mmHg. If vasopressor agent other than norepinephrine is being administered, then: order norepinephrine (Levophed), IV; set up IV infusion; after norepinephrine infusion set up is complete, D/C other vasopressor agent; increase or start norepinephrine (Levophed) dose rate by 5 mcg/min; IV; titrate dose rate to obtain 65≦MAP≦75 mmHg. If no vasopressor administration is ongoing, then measure MAP. If MAP≧55 mmHg, then go to step 420. If MAP<55 mmHg, then: order norepinephrine (Levophed), IV and set up IV infusion. After norepinephrine infusion set up is complete, D/C other vasopressor agent; increase (start) norepinephrine (Levophed) dose rate by 5 mcg/min; IV and titrate dose rate to obtain 65≦MAP≦75 mmHg.

At step 420 central venous and arterial catheters may be placed. Monitoring and antibiotic therapy started. More specifically in one embodiment the following actions are taken: If not present, place: 1) foley catheter (with T sensor); 2) peripheral arterial line; 3) central venous line (triple lumen) and 4) systemic oxygenation monitor (e.g. noninvasive tissue hemoglobin oxygen saturation, $StO_2$ monitor). If not ordered, order and obtain samples for clinical laboratory analyses: 1) peripheral blood culture (x3; 3 different sites; 20 mL/site); 2) [lactate]3) arterial blood gas analysis (measurements of: acid base balance, pH; partial pressure oxygen, PaO2, partial pressure carbon dioxide, PaCO2); 4) $Ca^{++}$, magnesium, phosphorus 5) complete blood count with differential WBC analysis; 6) international normalization ratio (INR), partial thromboplastin time (PTT), fibrinogen conentration ([fib]), D-dimer concentration; 7) cytokine+basic metabolic panel (BMP): IL-1ra, IL-6, IL-8, IL-10, ICAM-1, TNF-α, caspase-3, procalcitonin, K+, Na+, Cl—, [gluc], [creat], [BUN], [tot $CO_2$], [tot Ca]; 8) hepatic function panel; 9) thyroid function panel: T3, T4, TSH; 10) B-type natriuretic protein concentration (BNP); 11) C-reactive protein concentration (CRP); 12) blood type and screen (possible blood product transfusion); 13) urine screen; 14) if clinical pulmonary infection score (CPIS)>6, then perform mini bronchoalveolar lavage (BAL); or sputum culture if not intubated and 15) if patient is receiving vasopressor therapy, then order chest x ray. Probable source of infection and $StO_2$ are recorded, antibiotic agents (broad spectrum; IV) are given, the patient is screended for possible Xigris therapy. Order and obtain samples for clinical laboratory analyses: [lactate], arterial blood gas, INR, PTT, [fib], [D-dimer] and CBC with differential.

Additionally, in one embodiment the following actions may also be taken: blanket ICU consent obtained, or make chart entry explaining why consent could not be obtained. Pre printed orders signed and placed in chart. Notify intensivist physician when baseline monitoring is complete and document catheter placement procedures in chart. Antibiotic therapy may then be started, by recording a suspected or confirmed microorganism and selecting and administering the correct antibiotic agent from the table:

| Antibiotic drug | if severe Vancomycin allergy, then substitute Linezolid | Regimen 600 mg q12 hr |
|---|---|---|
| Indication | 1. 1$^{st}$ line<br>2. 2$^{nd}$ line | $^a$monitor, adjust for renal dysfxn<br>$^b$for severe β lactam allergies; kinetic monitoring |
| Pneumonia | | |
| Community acquired Aspiration | 1. Ceftriaxone + Azithromycin<br>2. Levofloxacin<br>Add Clindamycin or change Ceftriaxone to Piperacillin/ Tazobactam | 1 g IV q24 h<br>500 mg IV/PO q24 h<br>$^a$ 750 mg IV q24 h<br>600 mg IV q8 h<br>$^a$ 4.5 g IV q6 h |
| Ventilator associated | | |
| early (<5dy) | 1. Cefepime<br>2. Ciprofloxacin | $^a$ 2 g IV q12 h<br>$^a$ 400 mg IV q12 h |
| late (pseudomonas risk) | 1. Cefepime + Vancomycin + Tobramycin<br>2. Ciprofloxacin + Vancomycin + Clindamycin | $^a$ 2 g IV q24 h<br>$^a$ 15 mg/kg IV q12 h<br>$^{a,b}$ 7 mg/kg IV<br>$^a$ 400 mg IV q12 h<br>$^a$ 15 mg/kg IV q12 h<br>900 mg IV q8 h |
| Catheter related | | |
| Urinary catheter; UTI | 1. Piperacillin/ Tazobactam<br>2. Ciprofoxacin | $^a$ 4.5 g IV q6 h<br>$^a$ 400 mg IV q12 h |

-continued

| Antibiotic drug | if severe Vancomycin allergy, then substitute Linezolid | Regimen 600 mg q12 hr |
|---|---|---|
| IV, art cath; bloodstream Wound/Soft Tissue | Vancomycin | $^a$ 15 mg/kg IV q12 hr (after cath removal) |
| Necrotizing fasciitis | 1. Piperacillin/ Tazobactam + Vancomycin + Clindamycin | $^a$ 4.5 g IV q6 h $^a$ 15 mg/kg IV q12 h 900 mg IV q8 h |
| | 2. Ciprofloxacin + Vancomycin + Clindamycin | $^a$ 400 mg IV q12 h $^a$ 15 mg/kg IV q12 h 900 mg IV q8 h |
| Surgical site infection | 1. Piperacillin/ Tazobactam + Vancomycin | $^a$ 4.5 g IV q6 h $^a$ 15 mg/kg IV q12 h |
| | 2. Ciprofoxacin + Vancomycin | $^a$ 400 mg IV q12 h $^a$ 15mg/kg IV q12 h |
| Intra abdominal | 1. Imipenem/Cilistatin + Vancomycin +/- Fluconazole | $^a$ 500 mg IV q6 h $^a$ 15 mg/kg IV q12 h $^a$ 800 mg IV q24 h |
| | 2. Ciprofloxacin + Metronidazole + Vancomycin +/- Fluconazole | $^a$ 400 mg IV q12h 500 mg IV q8 h $^a$ 15 mg/kg IV q12 h $^a$ 800 mg IV q24 h |

At step 430 an effort is made to achieve hemodynamic stability. More specifically in one embodiment the following actions are taken: determine if steroid therapy is ongoing (pre or post hospital admit) and if steroid therapy is ongoing, then go to step 490. If steroid therapy is not ongoing, then go to step 430. Measure MAP and determine adrenal sufficiency. If MAP≧65 mmHg and vasopressor support ongoing, or if MAP<65 mmHg and vasopressor support not ongoing, then determine if adrenal stimulation test is complete, or if excluded as meaningful test. If no adrenal stim test exclusion criteria or if adrenal stim test complete and change in [cortisol]<9 µg/dL (results indicate adrenal insufficiency), then go step 490. If adrenal stim test exclusion criteria or if adrenal stim test complete and change in [cortisol]≧9 µg/dL (i.e. results indicate adrenal sufficiency), then determine hypotension: MAP<65 mmHg. If MAP<65 mmHg, then go to step 440. If MAP≧65 mmHg, then determine if norepinephrine infusion rate>0 (vasopressor support ongoing) or previous attempt to wean vasopressor support was >1 hr ago. If MAP≧65 mmHg, and if norepinephrine infusion rate=0 (no vasopressor support ongoing) or previous attempt to wean vasopressor support was <1 hr ago, then determine tachycardia: HR>120 bpm, or oliguria: UO<0.5 mL/kg-hr. If MAP≧65 mmHg, and if norepinephrine infusion rate>0 (vasopressor support ongoing) or previous attempt to wean vasopressor support was >1 hr ago, then go to step 440 (attempt to wean norepinephrine infusion rate to minimum dose rate to maintain MAP≧65 mmHg). If MAP 65 mmHg, and if norepinephrine infusion rate=0 (no vasopressor support ongoing) or previous attempt to wean vasopressor support was <1 hr ago, and if HR>120 bpm or UO<0.5 mL/kg-hr, then go to step 450.

At step 440 cardiac sufficiency may be determined. More specifically in one embodiment the following actions are taken: if CVP≧15 mmHg and norepinephrine dose rate≧15 µg/min, then go to step 402. If CVP<15 mmHg or norepinephrine dose rate<15 µg/min, then determine vascular volume and cardiac sufficiency: CVP≧10 mmHg. If CVP<10 mmHg, then go to step 450. If CVP≧10 mmHg and norepinephrine infusion rate=0 (or previously decreased within past hour to minimum necessary to maintain MAP≧65 mmHg), then determine hypotension: MAP<65 mmHg. If MAP<65 mmHg, then go to step 470. If MAP≧65 mmHg, and if norepinephrine infusion rate>0 (vasopressor support ongoing) or previous attempt to wean vasopressor support was >1 hr ago, then attempt to wean norepinephrine infusion rate to minimum dose rate to maintain MAP≧65 mmHg.

At step 450 fluid blood therapy may initiated. FIG. 5 depicts one embodiment of a segment of a protocol for sepsis diagnosis and management where the segment comprises rules for administering fluid or blood therapy. More specifically in one embodiment the following actions are taken: measure CVP and if CVP≧15 mmHg, then measure blood hemoglobin concentration ([Hb]). If [Hb]≧6 g/dL, then order 2 units PRBC. If CVP≧15 mmHg, then give 2 units IV over next hour. If CVP<15 mmHg, then give 2 units IV bolus (within 10 min; use pressure bag). If 6<[Hb]<8 g/dL, then order 1 unit PRBC and give IV bolus (within 5 min; use pressure bag). If CVP<15 mmHg, then determine if latest INR measurement≧6 hr old. If latest INR measurement≧6 hr old, then measure INR. If latest INR<6 hr old, then determine if latest INR≧2. If latest INR≧2, then determine if there is risk of hemorrhage or recent abdominal surgery. If hemorrhage risk or recent abdominal surgery, then determine if ≧4 units FFP were given. If ≧4 units FFP have not been given, then order and give 2 units FFP IV bolus (within 10 min; use pressure bag). After administration of 2 units FFP, re measure INR, and re measure CVP. If latest INR<2, or if no risk of hemorrhage or recent abdominal surgery, or if ≧4 units FFP have been given, then give 1 L LR IV bolus (within 5 min; use pressure bag). Measure CVP within 5 min of completion of IV infusion. If CVP<10 mmHg, then determine if ≧2 L LR have been given. If 2 L LR have not been given, then give $2^{nd}$ L LR IV bolus (within 5 min; use pressure bag). Measure CVP within 5 min of completion of IV infusion. If ≧2 L LR have been given, then measure [Hb]. If [Hb]≦6 g/dL, then order 2 units PRBC. If CVP>15 mmHg, then give 2 units PRBC IV over next hour. If CVP<15 mmHg, then give 2 units PRBC IV bolus (within 10 min; use pressure bag). If 6<[Hb]< 8 g/dL, then order 1 unit PRBC and give IV bolus (within 5 min; use pressure bag) or, if StO$_2$≧70%, if [Hb]<10, then order 1 unit PRBC and give IV bolus. If [Hb]≧8 g/dL (or ≧ 10), then go to step 460.

At step 460 systemic oxygen consumption may be assessed.

More specifically in one embodiment the following actions are taken: measure and record StO$_2$ and, if StO$_2$≧70%, then go to step 412. If time since start of sepsis protocol≧24 hr, then go to step 422. If time since start of sepsis protocol<24 hr, then go to step 432. If StO$_2$<70%, then determine if total isotonic fluid volume for last 6 hr (for example, fluid challenge 20 mL/kg+fluid therapy 2 L+other) given is >60 mL/kg ideal body weight. If total isotonic fluid volume>60 mL/kg, then determine if ≧2 L Hextend (hetastarch colloid balanced crystalloid solution; BioTime Inc) has been given in last 24 hr. If Hextend volume<2 L, then order and give Hextend 0.5 L IV bolus. Re measure and record StO$_2$. If StO$_2$≧70%, then go to step 412. If Hextend volume<2 L, then repeat Hextend 0.5 L IV bolus. Re measure and record StO$_2$. If StO$_2$≧70%, then go to step 412. If Hextend volume≧2 L, then determine persistent hypotension. If MAP<65 mmHg despite fluid challenge and fluid blood therapy interventions, then go to step 470. If StO$_2$<70% and total isotonic fluid volume (fluid challenge 20 mL/kg+fluid therapy 2 L+other) given for during administration of the protocol is 60 mL/kg ideal body weight, then reasses within 1 hour.

At step 470 vasopressor/inotrope therapy may initiated. FIG. 6 depicts one embodiment of a segment of a protocol for sepsis diagnosis and management where the segment comprises rules for administering vasopressor/inotrope therapy. More specifically in one embodiment the following actions are taken: If MAP<65 mmHg, determine if norepinephrine (Levophed) infusion is ongoing. If norepinephrine (Levophed) infusion is not ongoing, then start norepinephrine (Levophed) infusion, 6 μg/min, IV. Reassess MAP for effect of norepinephrine (Levophed) infusion in 5 min. If MAP<65 mmHg, then determine if norepinephrine (Levophed) infusion rate>15 μg/min.

If norepinephrine (Levophed) infusion rate<15 μg/min, then increase dose rate by 3 μg/min. Reassess MAP for effect of norepinephrine (Levophed) infusion rate increase in 5 min. If norepinephrine (Levophed) infusion rate≧15 μg/min, then notify an intensivist physician. If norepinephrine (Levophed) infusion rate≧15 μg/min, then determine if vasopressin infusion is ongoing. If vasopressin infusion is not ongoing, then start vasopressin infusion, 0.04 unit/min, IV. Reassess MAP for effect of vasopressin (and norepinephrine) infusion in 5 min.

If MAP<65 mmHg, norepinephrine (Levophed) infusion rate≧15 μg/min, and vasopressin infusion rate=0.04 unit/min are ongoing, then determine if an echo cardiogram was ordered and completed, and if results are available, and consult an intensivist physician to continue. If an echo cardiogram was not ordered, then order an echo cardiogram, and consult an intensivist physician to continue. If MAP<65 mmHg, norepinephrine (Levophed) infusion rate≧15 μg/min and vasopressin infusion rate=0.04 unit/min are ongoing, and if echo cardiogram results are available or pending, then, in consult with the intensivist, order increase of norepinephrine (Levophed) infusion rate by 3 μg/min increments with MAP reassessment after each increment to a maximum limit of 30 μg/min to obtain MAP≧65 mmHg, or order no further increase of norepinephrine (Levophed) infusion rate.

If MAP<65 mmHg, norepinephrine (Levophed) infusion rate≧15 μg/min (or 30 μg/min), and vasopressin infusion rate=0.04 unit/min are ongoing, and if no further increase of norepinephrine (Levophed) infusion rate is ordered, then assess echo cardiogram results and, in consult with SICU intensivist, assess systemic oxygenation (StO₂). If MAP<65 mmHg, norepinephrine (Levophed) infusion rate≧15 μg/min (or 30 μg/min), and vasopressin infusion rate=0.04 unit/min are ongoing, and if no further increase of norepinephrine (Levophed) infusion rate is ordered, then order increase of dobutamine infusion rate to obtain StO₂≧70%. If MAP≧65 mmHg with norepinephrine (Levophed) infusion rate<15 μg/min, or with norepinephrine (Levophed) infusion rate≧15 μg/min and vasopressin infusion=0.04 unit/min, then assess systemic oxygenation (StO₂). If StO₂<70%, then determine if dobutamine infusion is ongoing. If dobutamine infusion is not ongoing, then start dobutamine infusion, 2.5 μg/kg-min, IV.

Reassess MAP and StO₂ for effect of dobutamine infusion in 5 min. If StO₂<70%, then determine if dobutamine infusion rate≧10 μg/kg-min. If dobutamine infusion rate<10 μg/kg-min, then increase dose rate by 2.5 μg/kg-min. Notify an intensivist physician and reassess MAP and StO₂ for effect of dobutamine infusion rate increase in 5 min. If dobutamine infusion rate≧10 μg/kg-min, then consult an intensivist physician to continue. If MAP≧65 mmHg and StO₂≧70% with or without norepinephrine (Levophed) infusion, norepinephrine (Levophed) and vasopressin infusion, or dobutamine infusion, then re assess systemic oxygenation (StO₂) within 1 hr. If MAP<65 mmHg or StO₂<70%, norepinephrine (Levophed) infusion rate≧15 μg/min (or ≧30 μg/min) and vasopressin infusion=0.04 unit/min or dobutamine infusion rate≧10 μg/kg-min, then go to step 480.

At step 480 pulmonary artery catheter directed therapy may be initated. FIG. 7 depicts one embodiment of a segment of a protocol for sepsis diagnosis and management where the segment comprises rules for administering pulmonary artery catheter (PAC) directed therapy. More specifically in one embodiment the following actions are taken: an intensivist physician is notified and if the intensivist physician concurs, then order and place pulmonary artery catheter. If the intensivist physician does not concur with order to place pulmonary artery catheter, then instruction is provided to consider echo cardiogram and confirm whether steroid therapy ongoing.

In one embodiment, PAC directed therapy would proceed according to the protocol segment of FIG. 7, using [Hb], cardiac index (CI), and pulmonary capillary wedge pressure (PCWP) as the key measurement variables to guide protocol logic. Referring to FIG. 7, a PAC with continuous cardiac output (CCO) monitoring capability and an arterial catheter would be placed (A). Protocol logic would direct maintenance of DO₂≧500 mL O₂/min-m² (B) with interventions of: PRBC if [Hb]<10 g/dL and DO₂I<500 mL O₂/min-m²; crystalloid fluid bolus (LR, 1 L) if [Hb]≧10 g/dL, PCWP<15 mmHg, and DO₂I<500 mL O₂/min-m² (C); PCWP CI optimization ('Starling curve') if [Hb]≧10 g/dL, PCWP≧15 mmHg and DO₂I<500 mL O₂/min-m² (D); inotrope infusion (milrinone or dobutamine) if PCWP—CI was optimized, [Hb]≧10 g/dL, PCWP≧15 mmHg and DO₂I<500 mL O₂/min-m²; and, vasopressor infusion (norepinephrine) if inotrope infusion was ongoing, PCWP—CI was optimized, [Hb]≧10 g/dL, PCWP≧15 mmHg, DO₂I<500 mL O₂/min-m² and MAP<60 mmHg (E). (from Sucher et al. J Trauma 2008)

At step 490 adrenal insufficiency/steroid therapy may be administered. FIG. 8 depicts one embodiment of a segment of a protocol for sepsis diagnosis and management where the segment comprises rules for administering adrenal insufficiency/steroid therapy. More specifically in one embodiment the following actions are taken: determine if steroid therapy is ongoing. If steroid therapy is ongoing, then give 50 mg hydrocortisone IV bolus (Q 6 hr, 24 hr). Record: vasopressor dose rate, current MAP, when MAP<65 mmHg during past 6 hr, LR volume past 6 hr. If steroid therapy is not ongoing, then determine if vasopressor (Levophed/vasopressin) therapy is ongoing. If vasopressor therapy is ongoing, then determine if adrenal stimulation test is excluded as a meaningful test where exclusion criteria for adrenal stimulation test include: allergy to corticosteroid or adrenocorticotropic hormone (ACTH), steroid therapy in last 6 months, steroid therapy this hospital stay or etomidate in last 12 hours. If vasopressor therapy is not ongoing, then go to step 402. If vasopressor therapy is ongoing and if adrenal stimulation test is not excluded, then order adrenal stimulation test. Determine if latest [cortisol]≧6 hr old. If latest [cortisol]≧6 hr old, then order serum [cortisol] (random). Confirm that adrenal stimulation test is not complete. If adrenal stimulation test is not complete, then order and give 250 μg Cosyntropin IV; wait 30 min; order serum [cortisol] (random); wait additional 30 min; order 2$^{nd}$ serum [cortisol] (random); determine Δ[cortisol]= 1$^{st}$ or 2$^{nd}$ post Cosyntropin [cortisol]–pre Cosyntropin [cortisol]. If adrenal stimulation test is complete and Δ[cortisol]< 9 (i.e.+results, indicating adrenal insufficiency), then order and give 50 mg hydrocortisone IV bolus (Q 6 hr, 24 hr). Record: vasopressor dose rate, current MAP, when MAP<65 during past 6 hr, LR volume past 6 hr. If adrenal stimulation test is complete and Δ[cortisol]≧9 (i.e.—results, indicating adrenal sufficiency), then go to step 460.

At step 402 conventional therapies may have been maximized, thus criteria for recombinant activated protein C (Xigris) therapy may be assessed. More specifically in one embodiment the following actions are taken: confirm criteria for recombinant activated protein C (Xigris) therapy. If criteria met, then order and give recombinant activated protein C (Xigris). At step 412 hemodynamic stability may be assessed, and therapy given within 1 hr of change or previous assessment. At step 422 if 24 hours have elapsed since the start of the administration of the protocol, the protocol may be ended. Otherwise, at step 432: in reassess Q at 4 hours and reassess metabolic status (BMP), oxygenation (ABG), coagulation status (INR, PTT, [fib], [D dimer]), and blood cell counts.

As may be noted after a review of the protocol for the diagnosis and management of sepsis described above, the practical utilization of such a protocol may be relatively complex, as embodiments of these protocols may comprise many rules including many interventions. Thus, it is desirable from an implementation standpoint to provide effective methodologies or systems for the use of such protocols. Accordingly, in certain embodiments, a protocol, such as the embodiments of the sepsis diagnosis and management protocol described above, may be implemented in conjunction with a computer system which is tailored for use by a clinician in a health care environment.

More particularly, in one embodiment this computer implemented protocol may be configured to guide a clinician or other user through the implementation of a protocol such that requests for information, instructions for interventions or the presentation of information related to other rules associated with protocol may be delivered via computer to a interface and patient-specific data including patient responses to specific interventions or patient specific measurements may be obtained through an interface and rules of the protocol evaluated such that a subsequent instruction may be presented based both on the protocol being implemented by the computer system and the specifics of the patient whom the protocol is being utilized to treat.

Figure 10:
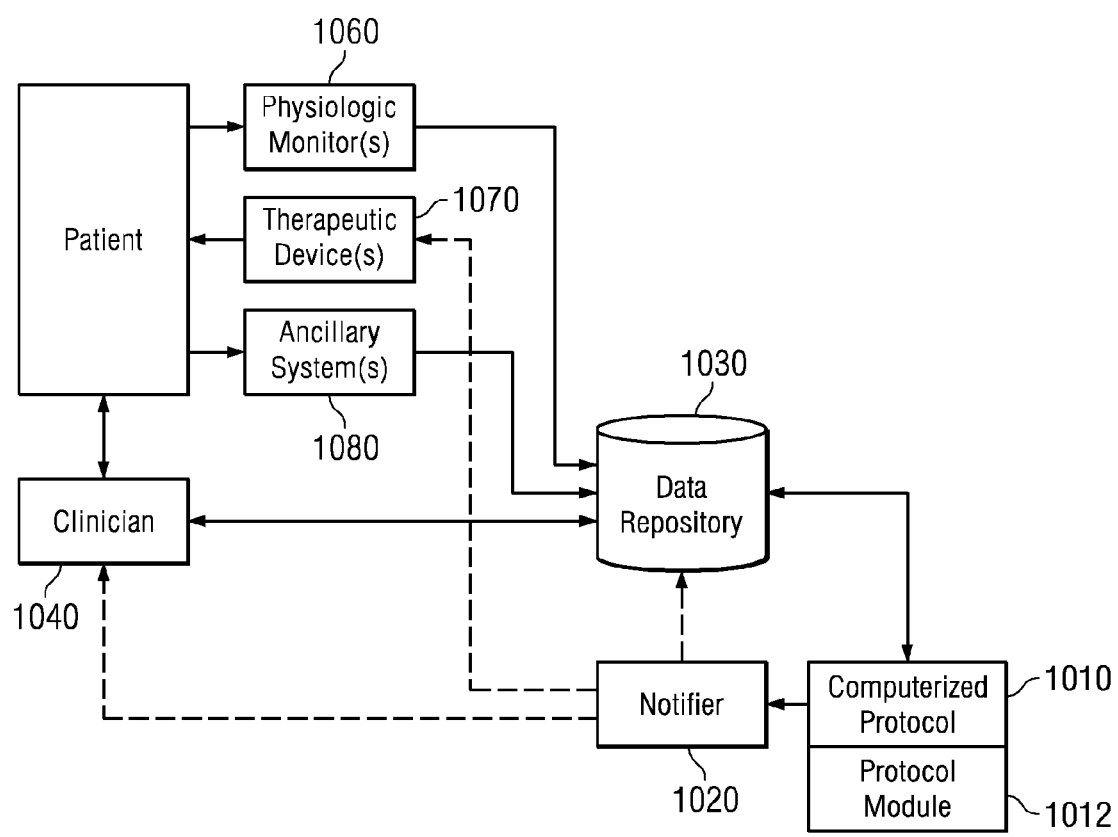
FIG. 10 is a block diagram of one embodiment of an architecture for the computerized implementation of a protocol.

FIG. 10 depicts one embodiment of a high-level architecture diagram for the implementation of a computer system implemented protocol for an aspect of care. A computerized protocol system 1010 may comprise a processor operable to execute a protocol implementation module 1012 configured to implement a protocol for an aspect of care. The computerized protocol may comprise one or more instructions stored on a tangible computer readable medium which are configured to implement a state machine or other program or logic according to the rules comprising the protocol for that aspect of care. Thus, protocol implementation module 1012 may deliver instructions to perform actions associated with the implementation of a protocol, including to ascertain and provide information, etc., through a notifier 1020 based on the rules comprising the protocol. This delivery may entail the presentation of certain displays or prompts on a visual, verbal or auditory interface device, etc. These actions may then be carried out by the clinician 1040 such that required therapeutic intervention or other action is performed on the patient, the proper information on the patient's current condition is ascertained, provided through the notifier and stored in the data repository 1050, etc.

Alternatively, the notifier 1020 may be linked to one or more medical devices such as physiological monitors 1060, therapeutic devices 1070 and any one of a number of ancillary systems 1080 such that at least one of the actions associated with protocol may be performed, information on the patient ascertained and stored in data repository 1050, etc. substantially without the involvement of clinician. For example, one or more medical devices in may be able to accept instructions in the Health Level 7 (HL7) Version 3 Messaging Standard messages and perform one or more actions based on the instructions or return data pertaining to the current state of the patient or other information to the data repository 1050. Thus, one or more instructions associated with the implementation of the protocol may be carried on substantially between the computerized protocol system 1010 and one or more medical devices 1060, 1070, 1080 substantially without any involvement by the clinician 1040

Figure 11:
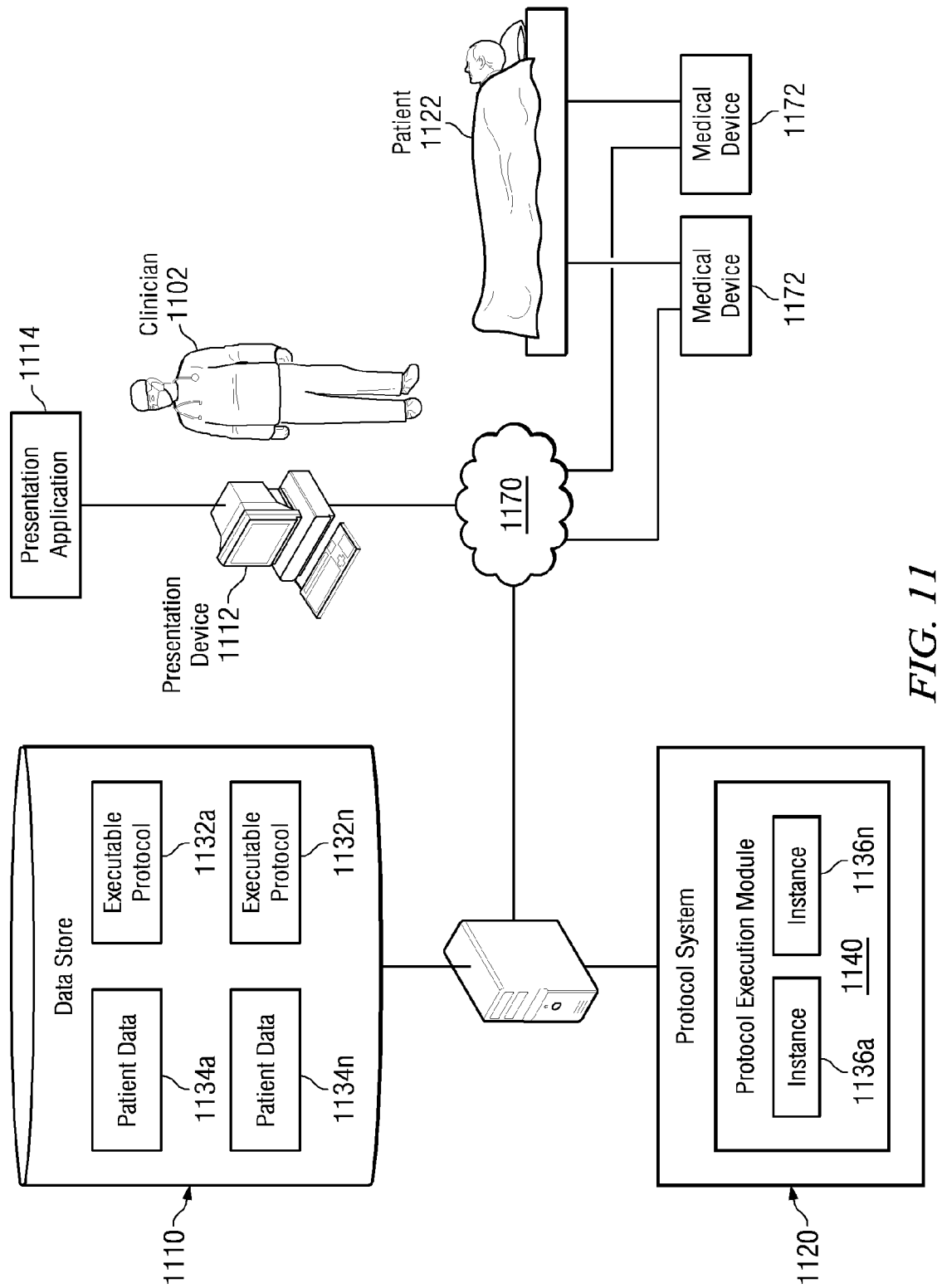
FIG. 11 a block diagram of one embodiment of an architecture for the computerized implementation of a protocol.
Figure 12A:
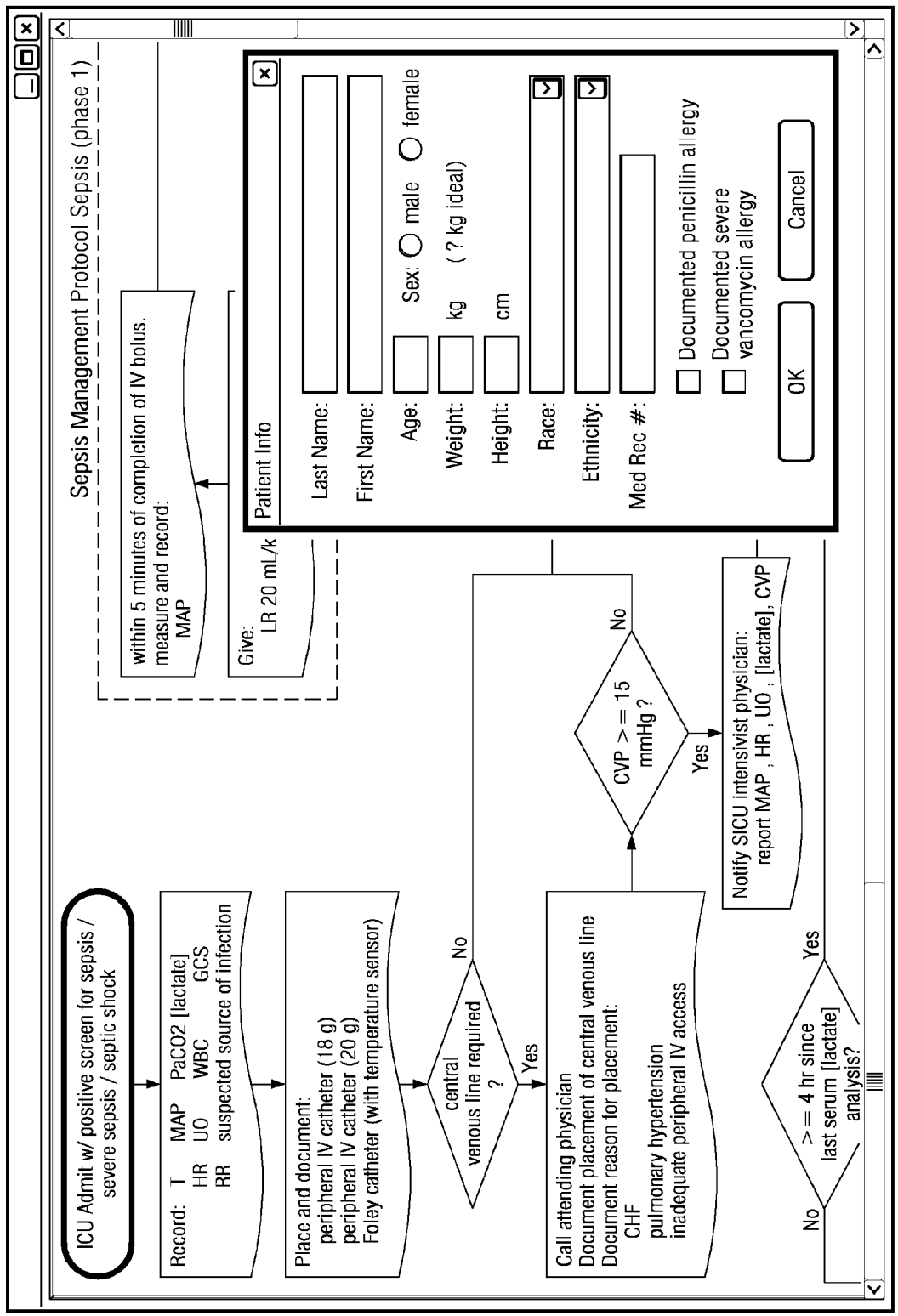
Figure 12C:
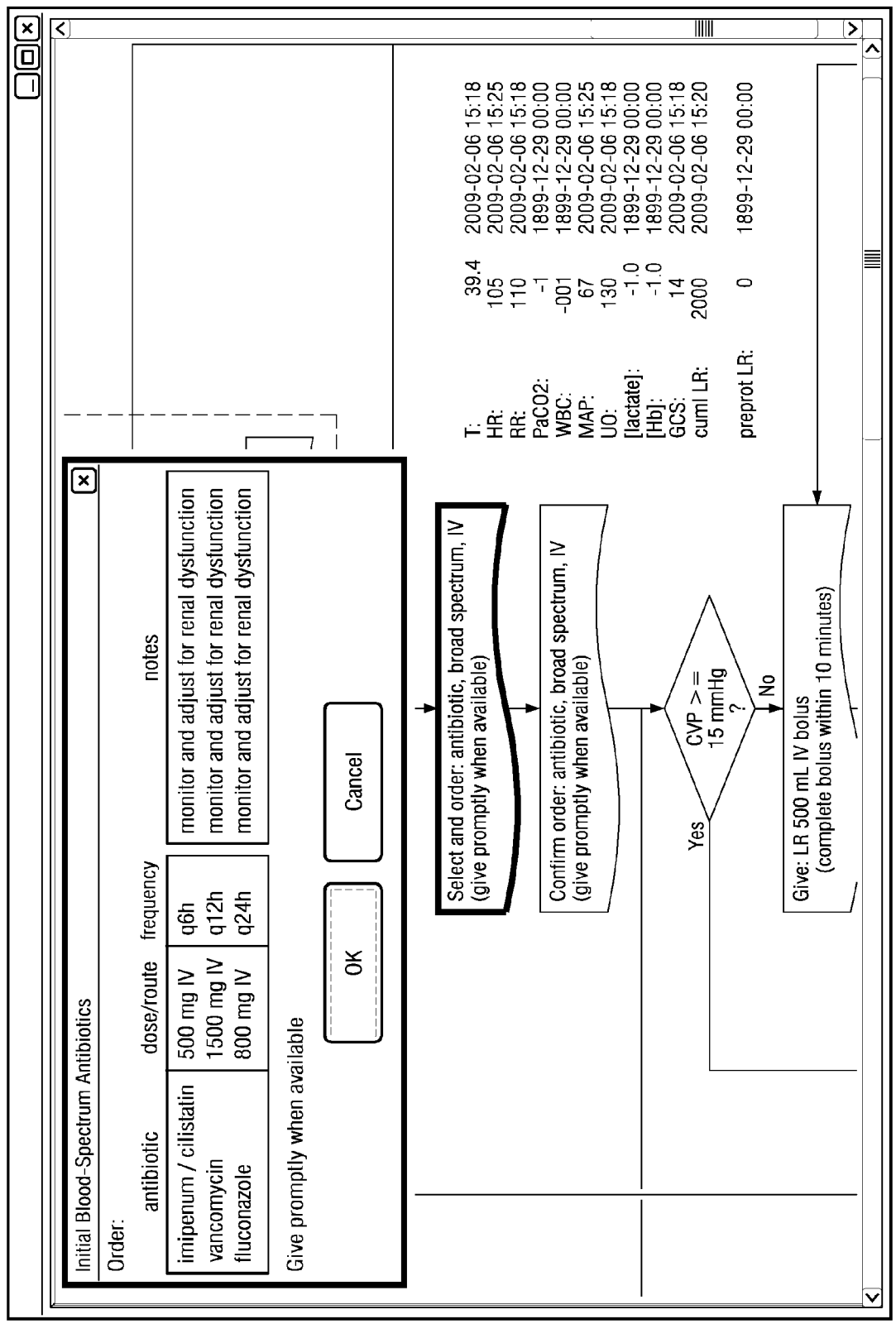
Figure 12D:
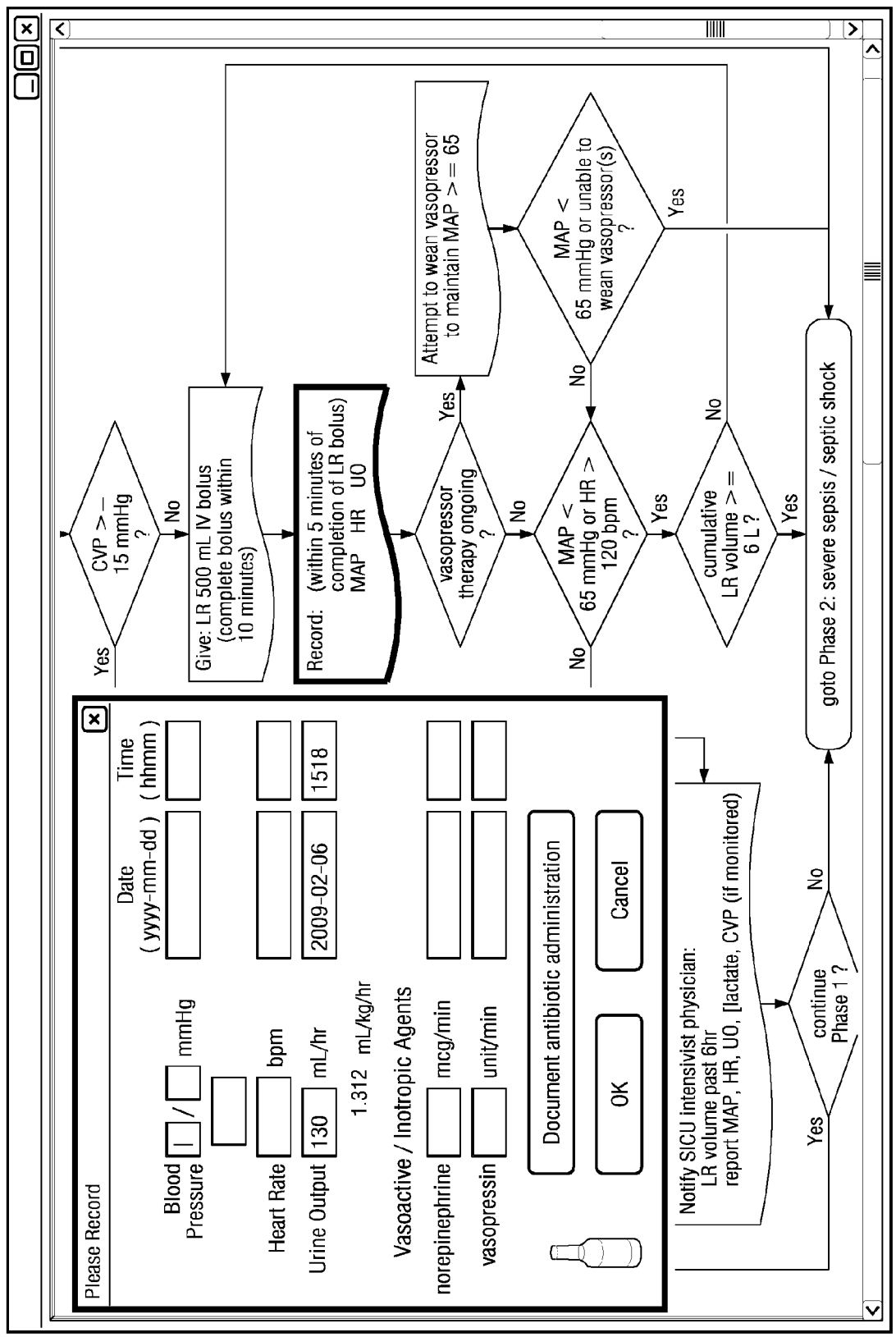
Figure 12E:
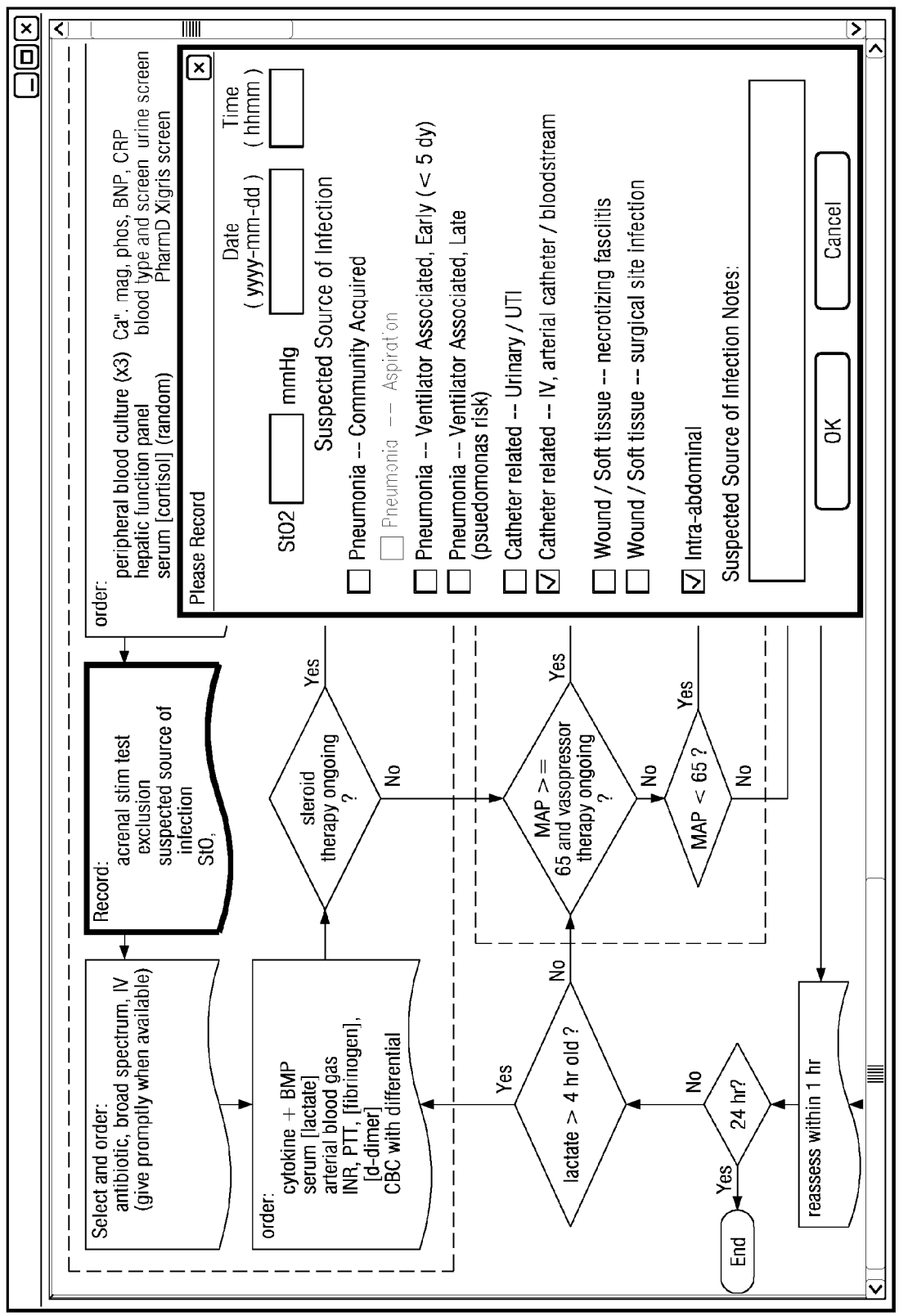

Referring now to FIG. 11, a more detailed depiction of the implementation of one embodiment of such a computerized protocol system, which may be utilized in conjunction with computerized implementation of protocols for aspects of care, including a protocol for the diagnosis and management of sepsis, is depicted. In particular, a clinical setting in which patient care is implemented, such as a hospital or the like may desire to implement protocols for one or more aspects of care being utilized to diagnose or treat patients. To that end, a protocol system 1120 may be employed in such a clinical setting to aid in the computerized implementation of such protocols.

Such a protocol system 1120 may be attached to a data store 1110, where the data store 1110 comprises a set of executable protocols 1132 and patient data 1134. An executable protocol 1132 may comprise a set of computer instructions configured to, when executed, implement a protocol, such as the protocol for the diagnosis and management of sepsis discussed above, in conjunction with one or more computer systems. Thus, protocol system 1120 may also comprise a protocol execution module 1140 executing on a processor of protocol system 1120 and configured to execute an executable protocol 1134 such that the protocol which the executable computer protocol is configured to implement may be utilized in conjunction with the care of a patient.

Specifically, in one embodiment, protocol system 1120 may be coupled through a wired or wireless communication network 1170, such as a LAN, WAN, Intranet, the Internet, etc. to one or more presentation devices 1112 (for example, computers, laptops, handheld devices, wireless handsets, mobile phones, etc.) residing in proximity to a patient 1122 such as in the patient's room, a unit of the clinical facility in which the patient resides, an operating room, etc. A presentation application 1114 configured to present one or more interfaces corresponding to the computerized implementation of a protocol may be executed by presentation device 1112.

It is desired to utilize a protocol corresponding to a particular aspect of care, a clinician 1102 may access protocol system 1120 utilizing presentation application 1114 on presentation device 1112 to select an executable protocol 1132 corresponding to the desired aspect of care it is desired to administer to patient 1122. The selected executable protocol 1132 may be executed by protocol execution module 1140 to implement the protocol in conjunction with the patient 1122. The execution of the executable protocol may comprise generating an instance 1136 of the selected executable protocol 1132, where the instance 1136 of the executable protocol 1132 comprises the rules and logic of the executable protocol 1132 plus a state corresponding to the currently selected rule of the protocol, where the instance 1136 of the executable protocol 1132 is associated with at least one set of patient data 1134 in the data store 1110.

The execution of the selected executable protocol 1132 comprises utilizing the instance 1136 to select an applicable rule and presenting one or more interfaces to the clinician 1102 on presentation device 1112 using presentation application 1114. These interfaces may include instructions for actions to be taken by clinician 1102 (for example, to be performed on, or in conjunction with patient 1122) or other types of instructions. These interfaces may also include requests to obtain data and provide associated interfaces to allow the clinician 1102 to enter the obtained information. The obtained data may then be stored in patient data 1134 corresponding to that instance 1136, such that a record is kept of data for that patient 1122 undergoing that particular protocol at that particular time period. Other data may also be stored in patient data 1134, for example, the logic or data that led to a particular rule being selected by protocol execution module 1140, the time certain actions occurred, patient-specific data (as non-limiting examples, demographics, criteria, related measurements, etc.) and patient responses to specific interventions. In some embodiments, the requested data may also be obtained automatically, from one or more medical devices 1172 coupled to the patient and to protocol system 1120 through network 1170.

Once the selected rule has been completed, protocol execution module may determine a subsequent rule based upon the state of the instance 1136 of the executable protocol 1136 and the patient data 1134 corresponding to patient 1122. Interfaces corresponding to the newly selected rule may then be presented through presentation device 1112. In this manner, a protocol for an aspect of care may be implemented on a computer system such that the rules of the protocol may be selected and implemented based on the state of a particular patient at a particular time period. This ability leads advantageously to clinically replicable care derived from currently known best practices and the like.

It will be apparent after a review of the above disclosure that a protocol for the diagnosis and management of sepsis, embodiments of which are discussed above may be advantageously implemented by a computer. It may be useful to illustrate examples of embodiments of visual interfaces which may be utilized by embodiments of a computerized protocol system configured to implement a protocol for the diagnosis and management of sepsis where the interfaces may be presented to a clinician to provide instructions to a clinician and provide interface to allow the clinician to provide information when prompted by the interface.

FIGS. 12A-12E depicts embodiments of such interfaces for a computer implemented protocol for the diagnosis and management of sepsis. More specifically, FIG. 12A one embodiment of an interface which may be utilized in association with rule similar to that of step 310 of FIG. 3 as discussed above is depicted, in FIG. 12B one embodiment of an interface which may be utilized in association with rule similar to that of step 320 of FIG. 3 as discussed above is depicted, in FIG. 12C one embodiment of an interface which may be utilized in association with rule similar to that of step 340 of FIG. 3 as discussed above is depicted, in FIG. 12D one embodiment of an interface which may be utilized in association with rule similar to that of step 360 of FIG. 3 as discussed above is depicted and in FIG. 12E one embodiment of an interface which may be utilized in association with rule similar to that of step 320 of FIG. 4 as discussed above is depicted Notice with respect to the various interfaces, that a flow diagram with representation of the rules of a protocol is displayed to a clinician or other user, with the currently selected rule highlighted. A "dialog box" comprising instructions to a clinician is also presented using the interface, where the dialog box comprises actions to be undertaken in conjunction with the selected rule, including actions to perform certain interventions or obtain certain information. Thus, utilizing these interfaces a clinician may be effectively guided through the implementation of a protocol with respect to an aspect of care in conjunction with administration of that aspect of care to a patient and in particular may be presented with rules and corresponding instructions for implementing a protocol for that aspect of care tailored to the state of a particular patient at a particular time.

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component of any or all the claims.

What is claimed is:

1. A system for computerized implementation of a protocol for diagnosis and management of sepsis, comprising:
   one or more presentation devices configured to present interfaces;
   a protocol system coupled to the one or more presentation devices, comprising:
      a processor;
      a data store;
      a computer readable medium comprising instructions executable by the processor for:
      implementing a replicable protocol for the diagnosis and management of sepsis comprising a first segment including a first set of rules corresponding to sepsis and a second segment including a second set of rules corresponding to severe sepsis, wherein the second set of rules are further segmented into a fluid/blood therapy segment, a vasopressor/inotrope therapy segment, an adrenal insufficiency/steroid therapy segment and a pulmonary artery catheter directed therapy segment; and
      implementing the protocol comprises:
         executing an instance of the protocol by a protocol execution module;
         determining a first rule of the protocol by the protocol execution module;
         presenting one or more interfaces corresponding to the first rule through a first presentation device, wherein the one or more interfaces comprises at least one request to obtain data corresponding to a patient;
         receiving the data associated with the first rule as implemented by a practitioner and corresponding to the patient at the protocol execution module from the first presentation device using the one or more interfaces;
         storing the data corresponding to the patient and associating the stored data with the instance of the protocol; and
         determining a second rule of the protocol based on the stored data corresponding to the patient and the instance of the protocol, wherein the second rule is determined by the protocol execution module.

2. The system of claim 1, wherein the first set of rules comprising the first segment comprises one or more rules for detecting sepsis.

3. The system of claim 2, wherein the one or more rules are configured to generate a score based on a heart rate, temperature, respiration rate and white blood cell count.

4. The system of claim 1, wherein the data corresponding to the patient is received from a medical device coupled to the patient and the protocol system.

5. A non-transitory computer readable medium comprising computer executable instructions, which when executed are configured to implement a protocol execution module of a protocol execution system, the protocol execution system coupled to at least one presentation device, the protocol execution module configured to:

execute an instance of a replicable protocol for the diagnosis and management of sepsis, wherein the protocol comprises a first segment including a first set of rules corresponding to sepsis and a second segment including a second set of rules corresponding to severe sepsis, wherein the second set of rules are further segmented into a fluid/blood therapy segment, a vasopressor/inotrope therapy segment, an adrenal insufficiency/steroid therapy segment and a pulmonary artery catheter directed therapy segment;

determine a first rule of the protocol;

present one or more interfaces corresponding to the first rule through a first presentation device, wherein the one or more interfaces comprises at least one request to obtain data corresponding to a patient;

receive the data associated with the first rule as implemented by a practitioner and corresponding to the patient from the first presentation device using the one or more interfaces;

store the data corresponding to the patient and associating the stored data with the instance of the protocol; and determine a second rule of the protocol based on the stored data corresponding to the patient and the instance of the protocol.

6. The computer readable medium of claim 5, wherein the first set of rules comprising the first segment comprises one or more rules for detecting sepsis.

7. The computer readable medium of claim 6, wherein the one or more rules are configured to generate a score based on a heart rate, temperature, respiration rate and white blood cell count.

8. The computer readable medium of claim 7, wherein the data is received from a medical device coupled to the patient and the protocol system.

9. A method implemented in a protocol execution module of a protocol execution system, comprising:

determining, at a protocol system including a processor, a first rule of a replicable protocol for the diagnosis and management of sepsis; wherein the protocol comprises a first segment including a first set of rules corresponding to sepsis and a second segment including a second set of rules corresponding to severe sepsis, wherein the second set of rules are further segmented into a fluid/blood therapy segment, a vasopressor/inotrope therapy segment, an adrenal insufficiency/steroid therapy segment and a pulmonary artery catheter directed therapy segment;

presenting one or more interfaces corresponding to the first rule through a first presentation device, wherein the one or more interfaces comprises at least one request to obtain data corresponding to a patient;

receiving the data associated with the first rule as implemented by a practitioner and corresponding to the patient from the first presentation device using the one or more interfaces;

storing the data corresponding to the patient and associating the stored data with the instance of the protocol; and determining, at the protocol system including the processor, a second rule of the protocol based on the stored data corresponding to the patient and the instance of the protocol.

10. The method of claim 9, wherein the first set of rules comprising the first segment comprises one or more rules for detecting sepsis.

11. The method of claim 10, wherein the one or more rules are configured to generate a score based on a heart rate, temperature, respiration rate and white blood cell count.

12. The method of claim 11, wherein the data is received from a medical device coupled to the patient and the protocol system.

\* \* \* \* \*